(12) United States Patent
Wong et al.

(10) Patent No.: US 7,177,452 B2
(45) Date of Patent: Feb. 13, 2007

(54) VISUALIZATION OF INFORMATION WITH AN ESTABLISHED ORDER

(75) Inventors: Pak Chung Wong, Richland, WA (US); Harlan P. Foote, Richmond, WA (US); James J. Thomas, Richland, WA (US); Kwong-Kwok Wong, Sugar Land, TX (US)

(73) Assignee: Battelle Memorial Institute, Richland, WA (US)

( * ) Notice: Subject to any disclaimer, the term of this patent is extended or adjusted under 35 U.S.C. 154(b) by 424 days.

(21) Appl. No.: 10/120,132

(22) Filed: Apr. 10, 2002

(65) Prior Publication Data

US 2003/0194116 A1    Oct. 16, 2003

(51) Int. Cl.
*G06K 9/00* (2006.01)

(52) U.S. Cl. ...................................... 382/128
(58) Field of Classification Search ................ 382/128
See application file for complete search history.

(56) References Cited

U.S. PATENT DOCUMENTS

| | | | | |
|---|---|---|---|---|
| 4,805,016 | A * | 2/1989 | Kato ........................... | 348/71 |
| 5,228,123 | A | 7/1993 | Heckel | |
| 5,416,848 | A | 5/1995 | Young | |
| 5,473,736 | A | 12/1995 | Young | |
| 5,583,973 | A | 12/1996 | DeLisi et al. | |
| 5,891,632 | A | 4/1999 | Imai | |
| 6,058,211 | A * | 5/2000 | Bormans et al. ............ | 382/235 |
| 6,151,595 | A | 11/2000 | Pirolli et al. | |
| 6,203,977 | B1 * | 3/2001 | Ward et al. .................... | 435/6 |
| 6,263,287 | B1 | 7/2001 | Zheng et al. | |
| 2001/0047376 | A1 | 11/2001 | Shaw | |

OTHER PUBLICATIONS

Hao, Bai-lin, "Fracals from genomes—exact solutions of a biology-inspired problem", Institue of Theoretical Physics, People's Republic of China, Feb. 1, 2000.*
Chi at el, "A Novel Visualization Method for biological Sequences Similarity", University of Minnesota, Nov. 30, 1999.*
Moon at el, "Analysis of the Clustering Properties of the Hilbert Space-Filling Curve", IEEE Transactions on Knowledge and Data Engineering, vol. 13, No. 1, Jan./Feb. 2001.*
Wong et al. "Global Visualization and Alignments of Whole Bacterial Genomes", Jul.-Sep. 2003, IEEE Transactions on Visualization and Computer Graphics, vol. 3, No. 3, pp. 361-377.*

(Continued)

*Primary Examiner*—Bhavesh M. Mehta
*Assistant Examiner*—Christopher Lavin
(74) *Attorney, Agent, or Firm*—Woodard, Emhardt, Moriarty and McNett & Henry LLP

(57) ABSTRACT

Among the embodiments of the present invention is a system including one or more processors operable to access data representative of a biopolymer sequence of monomer units. The one or more processors are further operable to establish a pattern corresponding to at least one fractal curve and generate one or more output signals corresponding to a number of image elements each representative of one of the monomer units. Also included is a display device responsive to the one or more output signals to visualize the biopolymer sequence by displaying the image elements in accordance with the pattern.

88 Claims, 21 Drawing Sheets

OTHER PUBLICATIONS

D.A. Keim, "Designing Pixel-Oriented Visualization Techniques: Theory and Applications, " IEEE Trans. Visualization and Computer Graphics, vol. 6, No. 1, Jan.-Mar. 2000.*

Lantin et al. "Supporting detail-in-context for the DNA representation, H-curves", Proceedings of the conference on Visualization '98, pp. 443-446.*

Keim, Daniel "Information Visualizatin and Visual Data Mining", IEEE Transactions on Visualization and Computer Graphics, vol. 8, No. 1, Jan.-Mar. 2002.*

Genome Image; htt://ivpr.cs.uml.edu/gallery/images/large/genome/Genome2.jpg; as least as early as Mar. 5, 2002.

Genome Image; htt://ivpr.cs.uml.edu/gallery/images/large/genome/Genome1.jpg; as least as early as Mar. 5, 2002.

Ashish Marnania, Georges Grinstein and Kenneth A. Marx, *GENVIS: A Sequence Visualization Technique for Genomic DNA*, University of Massachusetts at Lowell, SPIE vol. 2656, p. 189, (Date Unknown).

M.L. Lantin and M.S.T. Carpendale, "*Supporting Detail-in-Context for the DNA Representation, H-Curves,*" Simon Fraser University, (Date Unknown).

Dean F. Jerding and John T. Stasko, "*The Information Mural: A Technique for Displaying and Navigating Large Information Spaces*", Georgia Institute of Technology, Atlanta, GA., 1997.

Dean F. Jerding and John T. Stasko, "*The Information Mural*", Georgia Institute of Technology, Atlanta, GA., Mar. 1996.

H. Joel Jeffrey, "*Chaos game representation of gene structure*", Northern Illinois, University, DeKalb, Illinois, Nucleic Acids Research, vol. 18, No. 8, p. 2163, Mar. 20, 1990.

V.V. Solvovyev, S.V. Korolev, and H. A. Lim, "*A New Approach for the Classification of Functional Regions of DNA Sequences Based On Fractal Representations*", Int'l J. Genomic Res. 1:108-127, Russian Academy of Sciences & Florida State University, Jun. 3, 1991.

Ed Huai-hsin Chi, Phillip Barry, Elizabeth Shoop, John V. Carlis, Ernest Retzel, and John Riedl, "*Visualization of Biological Sequence Similarity Search Results,*" University of Minnesota, 1995.

Ed Huai-hsin Chi, Phillip Barry, Elizabeth Shoop, John V. Carlis, Ernest Retzel, and John Riedl, "*Flexible Information Visualization of Multivariate Data from Biological Sequence Similarity Searches*", University of Minnesota, 1996.

Peter Tiño and Georg Dorffiner, *Constructing finite-context sources from fractal representations of symbolic sequences*, Austrian Research Institute for Artificial Intelligence, 1998.

Guillermo Abramson, Hilda A. Cerdeira, and Carlo Bruschi, "*Fractal properties of DNA walks*", Int'l. Centre for Theoretical Physics and Int'l. Centre for Genetic Engineering and Biotechnology, Mar. 26, 1998.

Bai-lin Hao, H.C. Lee, and Shu-yu Zhang, "*Fractals related to long DNA sequences and complete genomes*", Chaos, Solitons and Fractals, Elsevier Science Ltd., 2000.

Peter Tiño "*Spatial Representation of Symbolic Sequences through Iterative Function Systems*", Austrian Research Institute for Artificial Intelligence, Austria, 1998.

Ed Huai-hsin Chi, Phillip Barry, Elizabeth Shoop, and John Riedl, "*A Novel Visualization Method for Biological Sequences Similarity*", University of Minnesota, Nov. 30, 1999.

Bai-lin Hao, "*Fractals from genomes—exact solutions of a biology-inspired problem*", Institute of Theoretical Physics, People's Republic of China, Feb. 1, 2000.

David B. Searls, "*Visualizing the Genome*", SmithKline Beecham Pharmaceuticals, (At least as early as Dec. 17, 2001).

R.A. Alm, L.S. Ling, D.T. Moir, B.L. King, E.D. Brown, P.C. Doig, D. R. Smith, B. Noonan, B.C. Guild, B.L. deJonge, G. Carmel, P.J. Tummino, A. Caruso, M. Uria-Nickelsen, D.M. Mills, C. Ives, R. Gibson, D. Merberg, S.D. Mills, Q. Jiang, D.E. Taylor, G.F. Vovis, T.J. Trust, "Genomic Sequence Comparison of Two Unrelated Isolates of the Human Gastric Pathogen *Helicobacter pylori,*" Nature, vol. 397, No. 6715, pp. 176-180, Jan. 1999.

S.F. Altschul, W. Gish, W. Miller, E.W. Myers, D.J. Lipman, "Basic local alignment search tool," *Journal of Molecular Biology*, vol. 215, No. 3, pp. 403-410, 1990.

A.R. Butz, "Alternative Algorithm for Hilbert's Space-Filling Curve," *IEEE Transactions on Computers*, vol. C-20, No. 4, pp. 424-426, Apr. 1971 (copy unavailable).

S.K. Card, J.D. Mackinlay, and B. Shneiderman, *Readings in Information Visualization—Using Vising To Think*, Morgan Kaufmann, 1999 (copy unavailable).

E.H. Chi, P. Barry, E. Shoop, J.V. Carlis, E. Retzel, and J. Riedl, "Visualization of Biological Sequences Similarity Search Results," *Proceedings IEEE Visualization 95*, pp. 44-51, IEEE Computer Society Press, Los Alamitos, CA, Oct. 1995.

E.H. Chi, J. Riedl, E. Shoop, J.V. Cartis, E. Retzel, and P. Barry, "Flexible Information Visualization of Multivariate Data from Biological Sequence Similarity Searches," *Proceedings IEEE Visualization 96*, pp. 133-140, ACM Press, NY, NY, Oct. 1996.

A.L. Delcher, S. Kasif, R.D. Fleischmann, J. Peterson, O. White, and S. Salzberg, "Alignment of Whole Genomes," *Nucleic Acids Research*, vol. 27, No. 11, pp. 2369-2376, May 1999.

L. Florca, C. Riemer, S. Schwartz, Z. Zhang, N. Stojanovic, W. Miller, and M. McClelland, "Web-based Visualization Tools for Bacterial Genome Alignments," *Nucleic Acids Research*, vol. 28, No. 18, pp. 3486-3496, Aug. 2000.

A.J. Gibbs and G.A. McIntyre, "The Diagram, A Method for Comparing Sequences. Its Use with Amino Acid and Nucleotide Sequences," *European Journal of Biochemistry*, vol. 16, pp. 1-11, 1970 (copy unavailable).

R.C. Gonzalez and R.E. Woods, *Digital Image Processing*, Addison Wesley, 1992 (copy unavailable).

E. Hamori and J. Ruskin, "H Curves, A Novel Method of Representation of Nucleotide Series Especially Suited for Long DNA Sequences," *The Journal of Biological Chemistry*, vol. 258, No. 2, pp. 1318-1327, Jul. 1983.

http://www.stat.duke.edu/courses/sta1xx/Data_sets/data_sets.html.

http://www.gcg.com/products/macvector.html.

http://www.ncbi.nlm.nih.gov.

http://www.tigr.org/tdb/mdb/mdb.html.

D. Jerding and J. Stasko, "The Information Mural: A Technique for Displaying and Navigating Large Information Spaces," *IEEE Transactions on Visualization and Computer Graphics*, vol. 4, No. 3, pp. 257-271, Jul. 1998.

S. Kalman, W. Mitchell, R. Marathe, C. Lammel, J. Fan, R. W. Hyman, L. Olinger, J. Grimwood, R. W. Davis, and R. S. Stephens, "Comparative genomes of *Chlamydia pneumoniae* and *C. trachomatis,*" *Nature Genetics*, vol. 21, No. 4, pp. 385-389, Apr. 1999.

D. A. Keim, "Designing Pixel-Oriented Visualization Techniques: Theory and Applications," *IEEE Transactions on Visualization and Computer Graphics*, vol. 6, No. 1, Jan. 2000.

D.A. Keim, H-P. Kriegel, and T. Seidl, "Visual Feedback in Querying Large Databases," *Proceedings IEEE Visualization 93*, pp. 158-165, IEEE CS Press, Los Alamitos, CA, Oct. 1993.

D.A. Keim, H-P. Kriegel, and M. Ankerst, "Recursive Pattern: A Technique for Visualizing Very Large Amounts of Data," *Proceedings IEEE Visualization 95*, pp. 279-286, IEEE CS Press, Los Alamitos, CA, Oct. 1995.

W. Kohler, *Gastalt Psychology: An Introduction to New Concepts in Modern Psychology*, Liveright, 1992 (copy unavailable).

A. Mamania, G. Grinstein, and K. Marx, "A Sequence Visualization Technique for Genomic DNA," *Proceedings of SPIE '96 Visual Data Exploration and Analysis Conference*, vol. 2656, pp. 189-199, 1996.

J. Parkhill, M. Achtman, K.D. James, S.D. Bentley, C. Churcher, S.R. Klee, G. Morelli, D. Basham, D. Brown, T. Chillingworth, R.M. Davies, P. Davis, K. Devlin, T. Feltwell, N. Hamlin, S. Holroyd, K. Jagels, S. Leather, S. Moule, K. Mungall, M.A. Quail, M.A. Rajandream, K.M. Rutherford, M. Simmonds, J. Skelton, S. Whitehead, B.G. Spratt, and B.G. Barrell, "Complete DNA Sequence of a Serogroup A Strain of *N. meningitidis* Z2491," *Nature*, vol. 404, No. 6777, pp. 502-506, Mar. 2000.

W.R. Pearson, "Comparison of methods for searching protein sequence databases," *Protein Sciences*, vol. 4, No. 6, pp. 1145-1160, Jun. 1995.

H-O. Peitgen, H. Jürgens, and D. Saupe, *Chaos and Fractals—New Frontiers of Science*, Springer-Verlag, New York, 1992 (copy unavailable).

J. Pustell and F. C. Kafatos, A Convenient and Adaptable Package of Computer Programs for DNA and Protein Sequence Management, Analysis, and Homology Determination, *Nucleic Acids Research*, vol. 12, pp. 643-655, 1984.

T.D. Read, R.C. Brunham, C. Shen, S.R. Gill, J.F. Heidelberg, O. White, E.K. Hickey, J. Peterson, T. Utterback, K. Berry, S. Bass, K. Linher, J. Weidman, H. Khouri, B. Craven, C. Bowman, R. Dodson, M. Gwinn, W. Nelson, R. DeBoy, J. Kolomay, G. McClarty, S.L. Salzberg, J. Eisen, and C.M. Fraser, "Genome Sequences of *Chlamydia trachomatis* MoPn and *Chlamydia pneumoniae* AR39," *Nucleic Acids Research*, vol. 28, No. 6, pp. 1397-1406, Jun. 2000.

S. Schwartz, Z. Zhang, K.A. Frazer, A. Smit, C. Riemer, J. Bouck, R. Gibbs, R. Hardison, and W. Miler, "PipMaker—A Web Server for Aligning Two Genomic DNA Sequences," *Genome Research*, vol. 10, No. 5, pp. 557-586, Apr. 2000.

M. Shirai, H. Hirakawa, M. Kimoto, M. Tabuchi, F. Kishi, K. Ouchi, T. Shiba, K. Ishii, M. Hattori, S. Kubara, and T. Nakazawa, "Comparison of whole genome sequences of *Chlamydia pneumoniae* J138 from Japan and CWL029 from USA," *Nucleic Acids Research*, vol. 28, No. 12, pp. 2311-2314, Jun. 2000.

M. Singer and P. Berg, *Genes & Genomes*, University Science Book, 1991 (copy unavailable).

E.L.L. Sonnhammer and J. C. Wootton, "Integrated Graphical Analysis of Protein Sequence Features Predicted From Sequence Composition," *PROTEINS: Structure, Function, and Genetics*, vol. 45, pp. 262-273, 2001.

R.S. Stephens, S. Kalman, C. Lammel, J. Fan, R. Marathe, L. Aravind, W. Mitchell, L. Olinger, R.L. Tatusov, Q. Zhao, E.V. Koonin, and R.W. Davis, "Genome Sequence of an Obligate Intracellular Pathogen of Humans: *Chlamydia trachomatis*," *Science*, vol. 282, No. 5389, pp. 754-759, Oct. 1998.

H. Tettelin, N.J. Saunders, J. Heidelberg, A.C. Jeffries, K.E. Nelson, J.A. Eisen, K.A. Ketchum, D.W. Hood, J.F. Peden, R.J. Dodson, W.C. Nelson, M.L. Gwina, R. DeBoy, J. D. Peterson, E.K. Hickey, D.H. Haft, S.L. Salzberg, O. White, R.D. Fleischmann, B.A. Dougherty, T. Mason, A. Ciecko, D.S. Parksey, E. Blair, H. Cittone, E.B. Clark, M.D. Cotton, T.R. Utterback, H. Khouri, H. Qin, J. Vamathevan, J. Gill J, V. Scarlato, V. Masignani, M. Pizza, G. Grandi, L. Sun, H.O. Smith, C.M. Fraser, E.R. Moxon, R. Rappuoli, and J.C. Venter, "Complete Genome Sequence of *N. meningitidis* Serogroup B Strain MC58," *Science*, vol. 287, No. 5459, pp. 1809-1915, Mar. 2000.

J.F. Tomb, O. White, A.R. Kerlavage, R.A. Clayton, G.G. Sutton, R.D. Fleischmann, K.A. Ketchum, H.P. Klenk, S. Gill, B.A. Dougherty, K. Nelson, J. Quackenbush, L. Zhou, E.F. Kirkness, S. Peterson, B. Loftus, D. Richardson, R. Dodson, H.G. Khalak, A. Glodek, K. McKenney, L.M. Fitzegerald, N. Lee, M.D. Adams, J.C. Venter, et al., "The Complete Genome Sequence of the Gastric Pathogen *Helicobacter pylori*," *Nature*, vol. 388, No. 6642, pp. 539-547, Aug. 1997.

D. Voorhies, "Space-Filling Curves and A Measure of Coherence," *Graphics Gems*, pp. 26-30, Academic Press, 1991 (copy unavailable).

M. Waterman, *Introduction to Computational Biology: Maps, Sequences and Genomes*, Chapman & Hall, New York, 1995 (copy unavailable).

N. Wirth, *Algorithms + Data Structures = Programs*, Prentice-Hall, 1976 (copy unavailable).

D. Wu, J. Roberge, D.J. Cork, B.G. Nguyen, T. Grace, "Computer Visualization of Long Genomic Sequences," *Proceedings IEEE Visualization 93*, pp. 308-315, IEEE CS Press, Los Alamitos, CA, Oct. 1993 (copy unavailable).

\* cited by examiner 510f  520f

VISUALIZATION OF INFORMATION WITH AN ESTABLISHED ORDER

GOVERNMENT RIGHTS

This invention was made with Government support under Contract DE-AC06-76R1-1830 awarded by the U.S. Department of Energy. The Government has certain rights in the invention.

BACKGROUND

The present invention relates to visualization of data, and more particularly, but not exclusively, relates to the visualization of biopolymer sequences comprised of different monomer unit types.

Recent success in the whole-genome shotgun sequencing effort has resulted in new opportunities and challenges in bioinformatic research. The genome of an organism is defined by one or more polynucleotide sequences. These sequences are typically comprised of four different types of organic nucleotide bases—Adenine, Cytosine, Guanine, and Thymine—with the total number of nucleotide bases ranging from hundreds of thousands found in bacteria to a few billion for human beings. Adenine, Cytosine, Guanine, and Thymine are commonly represented by the letters A, C, G, and T, respectively. Polynucleotide sequences are typically representative of ribonucleic acid (RNA) or deoxyribonucleic acid (DNA) molecules.

For a given organism, much of a genome is usually nonfunctional with the exception of most microbes. Nonfunctional sequence segments are often referred to as exons. The remaining functional sequence segments, generally referred to as introns, provide genes to encode various sequences of amino acids, producing corresponding proteins (polypeptides). Specifically, three consecutive nucleotide bases of a genetic sequence (a codon) encode one amino acid of a protein. Such proteins, generally in the form of an enzyme, serve as the building blocks of various biologic processes.

As genome and/or protein sequence information accumulates, there is an increasing interest in different ways to analyze such information. One area of particular interest is the comparison of different genomes to identify genes that are responsible for different characteristics of the corresponding organisms. To perform such comparisons, the genomes are aligned with respect to common reference points.

While many organisms—including human beings—have genomes arranged in an open loop with ends that commonly serve as reference points for such alignments, other organisms—including various bacteria—have genomes arranged in a closed loop. This closed loop arrangement can make it relatively more difficult to perform alignments of bacteria genomes. In many cases, minor genomic variations between two bacteria strains may reflect significant differences in their overall characteristics. For example, even though *Escherichia coli* (*E. coli*) strain O-157 shares over 90% of sequence homology with *E. coli* strain K-12, the former is notoriously fatal while the latter is completely harmless to humans.

Various software tools based on dynamic programming and hashing, such as BLAST and FASTA, have been developed to align sequences. These tools are sometimes used to compare sequences with tens of thousands of biomonomer units, as might be found in a single protein or intron segment. However, the performance of such tools often degrades significantly when whole genomes with millions of nucleotides are involved. Furthermore, these tools generally only compare two sequences at a time.

Besides biopolymer sequences, complex polymers comprised of different monomer unit types could also benefit from different evaluation techniques. Moreover, other types of data having an "a priori" order, such as time-series data to name just one example, can benefit from techniques to process large data sequences.

Thus, there is a need for better ways to focus existing analytic tools on those parts of a genome sequence that are of interest. More generally, there is an ongoing need for better ways to evaluate complex polymer sequences comprised of different monomer unit types and/or other data having an a priori order.

SUMMARY

One embodiment of the present invention includes a unique technique for data visualization. Other embodiments include unique methods, systems, devices, and apparatus for visualizing information.

In a further embodiment, a visualization of a biopolymer sequence is provided. The visualization can be provided by representing the biopolymer sequence of monomer units with a number of image elements each having an appearance that varies with different monomer unit types. One or more routines can be performed to arrange these image elements in a form desirable to visualize the sequence. Moreover, this sequence can be compared to sequences for other biopolymers to visually identify homologous and/or nonhomologous segments.

Another embodiment includes: selecting a biopolymer sequence of at least 100,000 monomer units each being one of at least two different types; representing this sequence with at least 100,000 image elements that vary in appearance with the different types; and displaying the image elements in a pattern arranged to visualize the sequence.

Yet another embodiment of the present invention includes displaying a first visualization of a first genetic sequence and a second visualization of a second genetic sequence. The first and second visualizations each include a pattern corresponding to a fractal curve. A comparison of these patterns is performed and the first genetic sequence and second genetic sequences are aligned based on this comparison.

In still another embodiment, a biopolymer sequence of monomer units is represented with a number of image elements that each correspond to one of the monomer units and vary in color with different monomer unit types. A routine to enhance colorization of the image elements is performed and an image is displayed including these elements arranged in an order corresponding to the sequence. This routine can include adjusting the coloration with histogram equalization.

In another embodiment, a device carries instructions executable with computer equipment to access data corresponding to a biopolymer sequence. These instructions are further executable with the computer equipment to represent the sequence with image elements that vary in appearance with different types of monomer units comprising the sequence and to display an image including the image elements arranged in an established pattern to visualize the sequence.

Another embodiment of the present invention includes: selecting a biopolymer sequence of at least 100,000 monomer units that are each one of a number of different types; providing a visualization image including at least 100,000 image elements to represent sequence; and spatially ordering the image elements in accordance with monomer unit order of the sequence. The image elements can each represent at least one of the monomer units with one of a number of appearances that differ with the different types of the monomer units.

In another embodiment, a visualization of a biopolymer sequence of monomer units is generated and the sequence is represented in the visualization with a sequence of image elements spatially ordered in accordance with a repeating folded line segment pattern. Alternatively or additionally, the image elements can be arranged in a spatial order that progresses relative to a turning path where one portion of the path proceeds in a first direction and another portion of the path proceeds in a second direction opposite the first direction.

Yet another embodiment of the present invention includes selecting a display pattern to represent a biopolymer sequence, where such pattern corresponds to a fractal with a fractal dimension of two. A matrix of display locations is at least partially filled in accordance with the display pattern to visualize the biopolymer sequence. In one form, the fractal corresponds to at least one of a Hilbert curve and a Moore curve.

A further embodiment includes selecting a sequence of nucleotide bases and providing a visualization of the sequence of nucleotide bases with a corresponding sequence of image elements. The image elements each correspond to one of the bases and vary in color with different nucleotide base types and the visualization includes a first area with one coloration surrounded by a second area of a different coloration. The first area represents one sequence segment of at least 1,000 nucleotide bases and the second area represents one or more other sequence segments.

For yet a further embodiment, a first visualization is displayed including a first image element sequence to represent a nucleotide base sequence defining a first genome and a second visualization is displayed including a second image element sequence to represent another nucleotide base sequence defining a second genome. The first and second visualizations are compared and one of the image element sequences is realigned based on this comparison.

In still other embodiments, various systems, computer equipment, and computer instruction carrying apparatus are provided to perform one or more of the previously described embodiments. Still other embodiments of the present invention provide visualizations of entire genome sequences or large segments thereof numbering at least several hundred thousand nucleotide bases in length.

One object of the present invention is to provide a unique technique for data visualization.

Another object of the present invention is to provide a unique method, system, device, or apparatus for visualizing information.

Further embodiments, forms, features, aspects, benefits, objects, and advantages shall become apparent from the detailed description and figures provided herewith.

DETAILED DESCRIPTION

Figure 1:
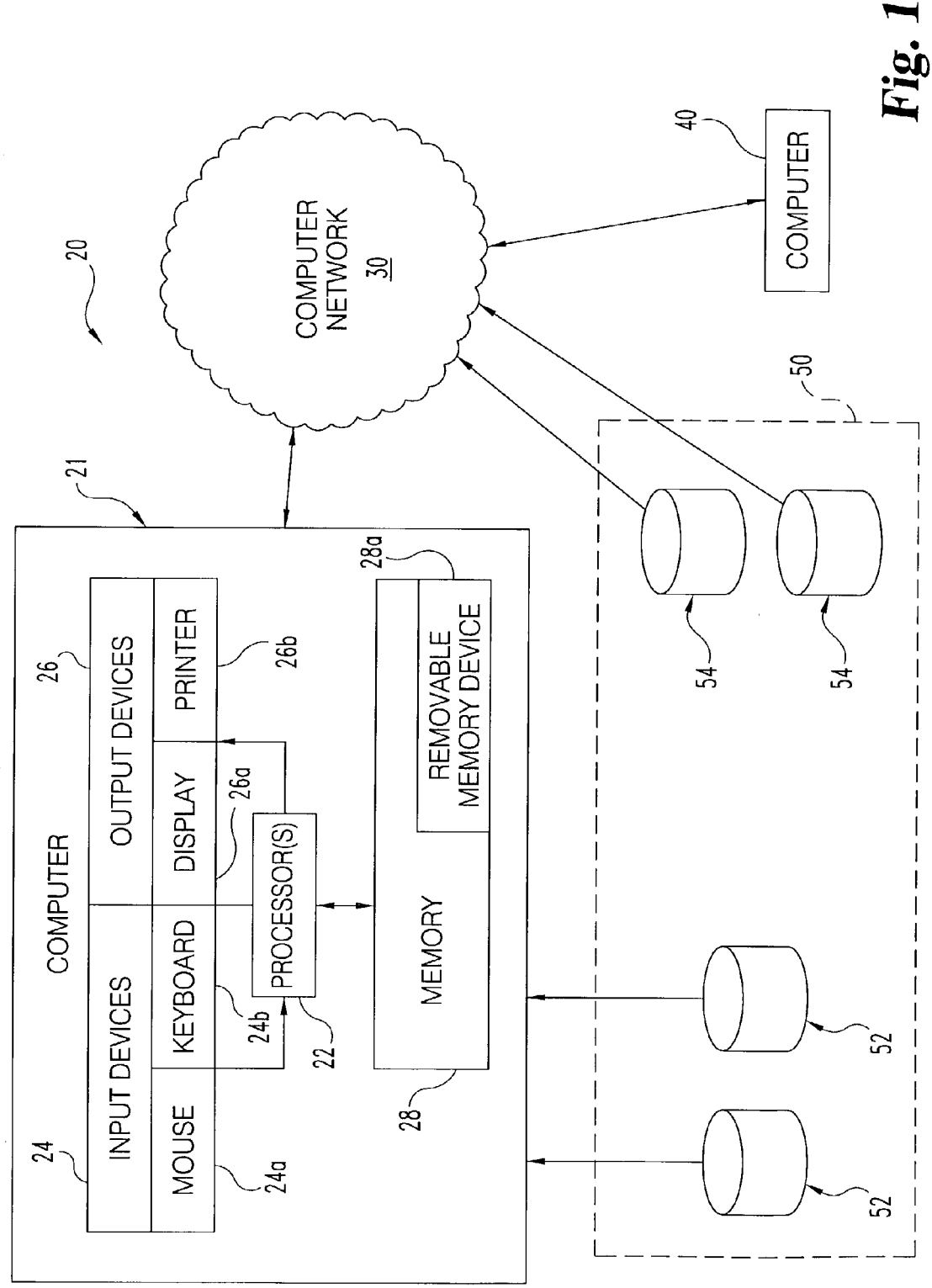
FIG. 1 is a diagrammatic view of a computing system.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Among the embodiments of the present invention is a unique technique to visualize biopolymer sequences comprised of two or more different types of monomer units. This technique can include visualizing the sequence with a number of image elements each representing at least one of the monomer units and having an appearance indicative of the monomer unit type or types represented. In one form, image element appearance chromatically and/or achromatically varies in color with the different monomer unit types represented. The image elements can be displayed in a spatially ordered pattern corresponding to monomer unit order of the sequence. In one form, this pattern corresponds to a fractal having a fractal dimension of at least two. Alternatively or additionally, one or more image enhancement procedures can be applied as part of this technique, such as image filtering, histogram equalization, contrast stretching (normalization), and saturation adjustment to name just a few.

Using such techniques, visualization of different genetic sequences can be prepared and compared to identify one or more similarities and/or differences. In a further embodiment, alignment of different bacterial genomes is facilitated through such processing. In still other embodiments, various unique systems, devices, and apparatus are provided. By way of nonlimiting example, FIG. 1 diagrammatically depicts processing system 20 of another embodiment of the present invention.

System 20 includes computer equipment 21 with one or more computer processor(s) 22. System 20 also includes operator input devices 24 and operator output devices 26 operatively coupled to processor(s) 22. Input devices 24 include a conventional mouse 24a and keyboard 24b, and alternatively or additionally can include a trackball, light pen, voice recognition subsystem, and/or different input device type as would occur to those skilled in the art. Output devices 26 include a standard graphic computer monitor display 26a and printer 26b, and alternatively or additionally can include an aural output system, and/or different output device type as would occur to those skilled in the art. In one embodiment, computer monitor display 26a is of a Cathode Ray Tube (CRT), Liquid Crystal Display (LCD), plasma, or different graphic computer monitor display type as would occur to those skilled in the art; and printer 26b is of an impact, ink-jet, laser, or different type as would occur to those skilled in the art. These devices sometimes can be characterized as having a matrix of display locations. By way of nonlimiting example, a computer monitor CRT type display that has 1600×1200 addressable pixels can be considered to have a 1600×1200 matrix of display locations. Further, in other embodiments, more or fewer operator input devices 24 or operator output devices 26 may be utilized.

Processor(s) 22 can be comprised of one or more integrated circuit components of a digital type, analog type, or a hybrid combination of these. Processor(s) 22 broadly refer to any data or instruction processing circuitry and/or device(s), signal conversion/conditioning circuits, power supplies, and/or different circuits, devices or arrangements as would occur to those skilled in the art to implement the present invention. For one embodiment, processor(s) 22 are based on at least one microprocessor of a standard variety. Embodiments including multiple processor(s) 22 can be arranged with two or more of processors 22 in a single computer unit, and/or two or more processors 22 each in different units configured for distributed processing. In one form, processor(s) 22 are programmed with software instructions that are executed to perform various desired operations. In other forms, some or all of the logic executed by processor(s) 22 through software programming is replaced with firmware; dedicated hardware, such as hardwired digital and/or analog circuitry; and/or using such different techniques as would occur to one skilled in the art. Some or all processor operations may be executed with a single processor, two or more processors operating in parallel, two or more processors operating on data in series (or in "pipeline" arrangement), a combination of these, and/or using different techniques known to those skilled in the art.

System 20 also includes memory 28 operatively coupled to processor(s) 22. Memory 28 can be of one or more types, such as solid-state electronic memory, magnetic memory, optical memory, or a combination of these. As illustrated in FIG. 1, memory 28 includes a removable/portable memory device 28a that can be an optical disk (such as a CD ROM or DVD); an electromagnetically encoded hard disk, floppy disk, tape, or cartridge media; or a different form as would occur to those skilled in the art. In one embodiment, at least a portion of memory 28 is operable to store programming instructions for processor(s) 22. Alternatively or additionally, memory 28 can be arranged to store data other than programming instructions for processor(s) 22. In still other embodiments, memory 28 and/or portable memory device 28a may not be present. In one such example, a hardwired state-machine configuration of processor(s) 22 does not utilize memory-based instructions.

System 20 also includes computer network 30 that can include a Local Area Network (LAN); Wide Area Network (WAN), such as the Internet; another type as would occur to those skilled in the art; or a combination of these. Network 30 couples computer 40 to computer equipment 21; where computer 40 is remotely located relative to computer equipment 21. Computer 40 can include one or more processor(s), input devices, output devices, and/or memory as described in connection with computer equipment 21; however these features of computer 40 are not shown to preserve clarity of FIG. 1.

Computer 40 and computer equipment 21 can be arranged as client and server, respectively, in relation to some or all of the data processing of the present invention. For this arrangement, it should be understood that many other remote computers 40 could be included as clients of computer equipment 21, but are not shown to preserve clarity. In another embodiment, computer equipment 21 and computer 40 can both be participating members of a distributed processing arrangement utilizing at least one processor of each site. The distributed processors 22 of such an arrangement can be used collectively to execute routines according to the present invention. In still other embodiments, remote computer 40 and/or computer network 30 may be absent.

System 20 is also depicted with computer-accessible data sources 50. Sources 50 include databases 52 local to computer equipment 21 and remotely located databases 54 accessible via network 30. Computer equipment 21 is operable to process data selected from one or more of sources 50. Sources 50 may be comprised of memory of any of the types described in connection with memory 28 and/or such other type as would occur to one skilled in the art. Sources 50 can further include other computer processing devices, servers, and the like to facilitate the present invention. In one form, sources 54 include publicly available genome sequences accessible via the world wide web.

Figure 2:
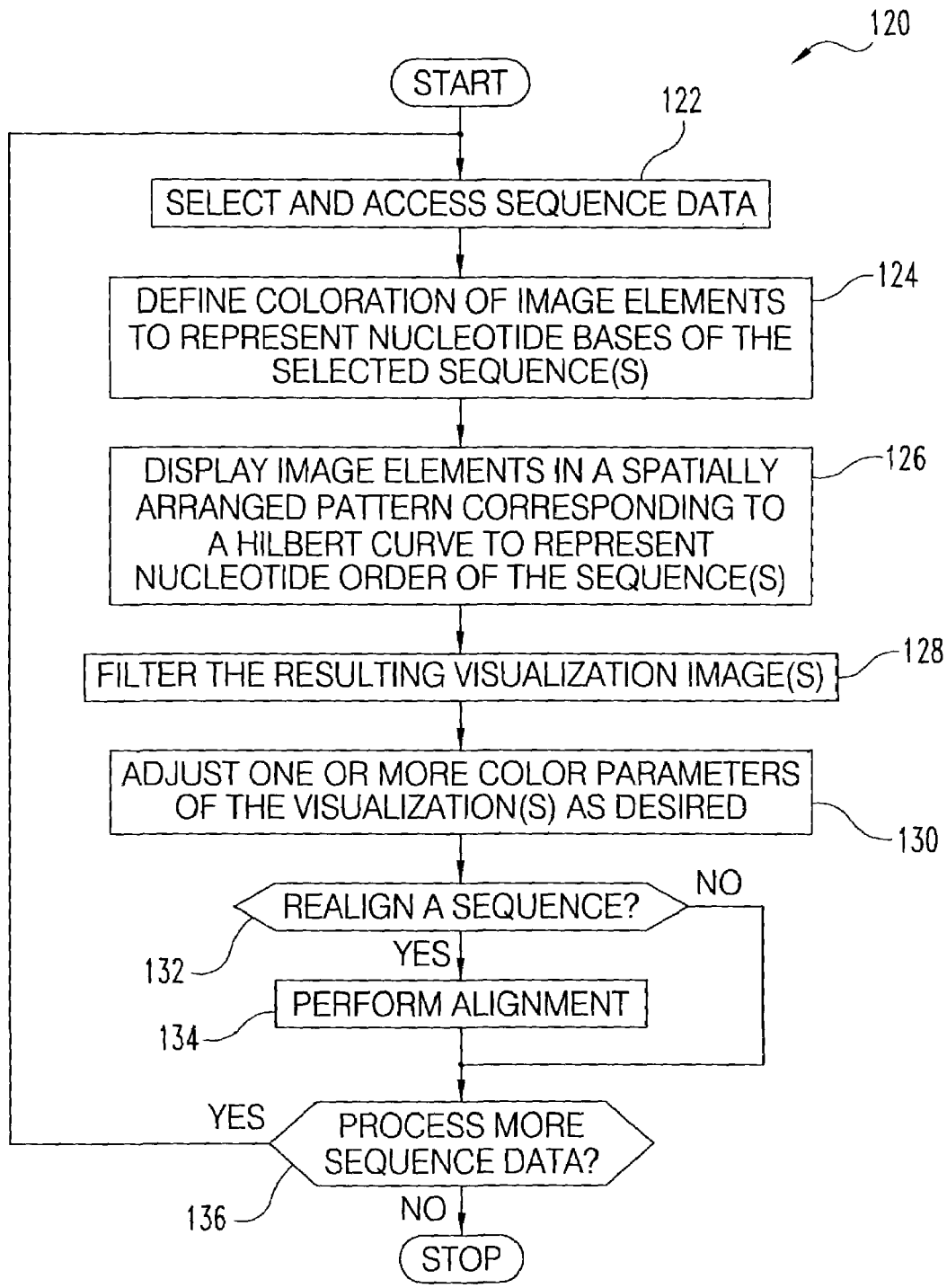
FIG. 2 provides a flowchart illustrating details of a visualization process that can be executed with the system of FIG. 1.

Referring additionally to FIG. 2, visualization routine 120, that can be implemented with system 20, is illustrated in flow chart form. Routine 120 generates visualizations of the type shown in FIGS. 7, 10–16 and 18–22 to represent data having an a priori order as further described hereinafter. At least a portion of this visualization generation can be performed with software, firmware, and/or hardware of computer equipment 21. Such visualizations can be presented on display 26, printer 26b, and/or can be transmitted remotely to other devices, such as computer 40, for display or further processing.

Routine 120 begins in stage 122. In stage 122, computer equipment 21 is used to select and access genome sequence data from one or more of memory 28 and/or sources 50. The stage 122 selection and access corresponds to one or more genomes or genome segments of interest. In the case of multiple genomes or segments, routine 120 can generate a separate visualization for each. Computer equipment 21 initially generates a visualization image by representing each nucleotide base of the selected sequence or sequences with a corresponding image element. The image elements can each be the smallest addressable unit of display device 26a and/or printer 26b, be multiples of such units, be a virtual object that can be assigned different visual forms, and/or a combination of these. For an example of display 26a with 1600×1200 addressable pixels, about 2 million image elements could be presented; where each image element corresponds to a different pixel. In other examples, a different number of image elements and/or ratio relative to the number of pixels could be utilized.

Routine 120 proceeds from stage 122 to stage 124. In stage 124, a different color is assigned to each image element based on the type of nucleotide base it represents. For example, image elements representing A, C, G, T can correspondingly be white, yellow, orange, and brown (e.g. a hot temperature mapping); or red, lavender, light blue, and dark blue (e. s. a cold temperature mapping). In other examples, a different chromatic color assignment or an achromatic color assignment can be used. Alternatively or additionally, different image element shapes, sizes, etc. can be assigned to vary image element appearance in correspondence to the different nucleotide bases represented. Assignment of different appearances to the image elements in this manner creates an image element sequence that reflects the order of the different nucleotide base types in the genomic sequence.

From stage 124, routine 120 continues with stage 126. In stage 126 image elements are presented in a display field of display 26a and/or printer 26b in a spatial order corresponding to the nucleotide base order. This spatial order is provided in accordance with a pattern corresponding to a finite portion of a Hilbert curve. A Hilbert curve is a type of fractal that is self-similar at $2^n \times 2^n$ (n=1, 2, 3 . . . ) and has a fractal dimension of two; where n is an integer scale factor and n=1 corresponds to the fundamental motif of this fractal in terms of a square two by two matrix.

Figure 3:
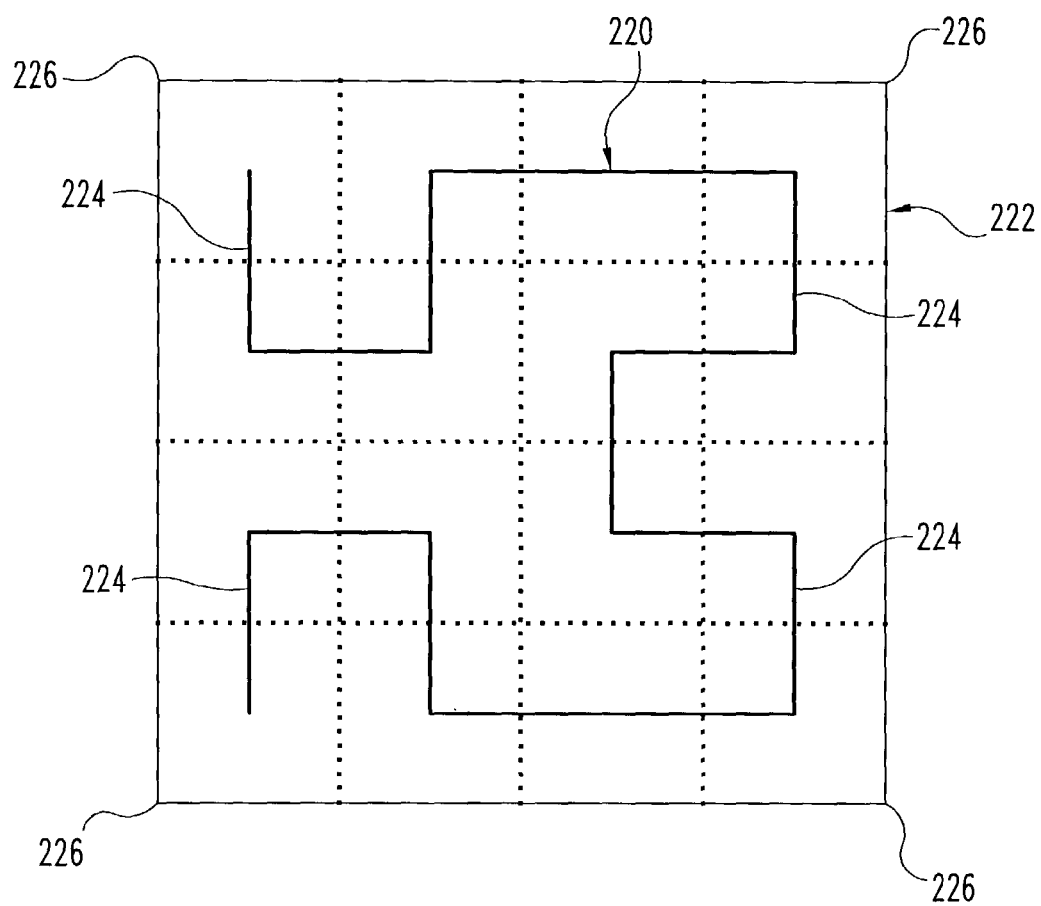
FIGS. 3, 4, and 5 are views of Hilbert curve diagrams corresponding to progressively larger matrices.
Figure 4:
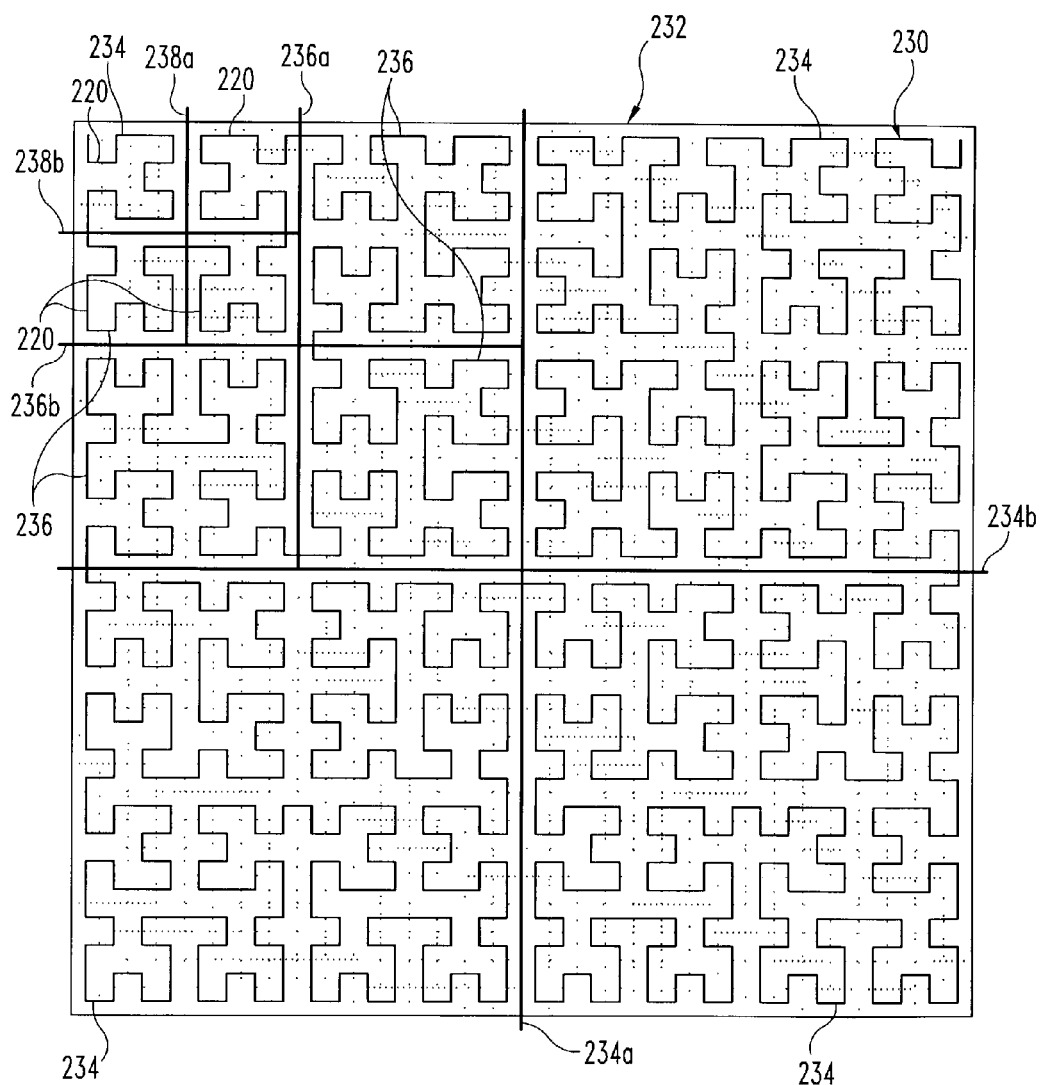

Referring to the example of FIG. 3, Hilbert curve 220 for n=2 is illustrated relative to a square 4 by 4 matrix 222. Matrix 222 is outlined by solid lines and its 16 locations are depicted with a broken line grid. The folded solid, line segment 224 repeated four times in curve 220 corresponds to the motif of n=1 relative to a corresponding one of 4 two-by-two submatrices 226 of matrix 222. Referring additionally to FIG. 4, Hilbert curve 230 for n=5 is illustrated relative to a square 32 by 32 matrix 232, with locations of matrix 232 being depicted by the same broken line grid arrangement as for matrix 222. Perpendicular symmetry lines 234a and 234b intersect one another to divide curve 230 into four solid, folded line segments 234 each corresponding to a Hilbert curve for n=4. Segment 234 in the upper left corner is further divided by perpendicular, intersecting symmetry lines 236a and 236b, revealing four smaller folded line segments 236 each corresponding to a Hilbert curve for n=3. In turn, perpendicular symmetry lines 238a and 238b intersect one another to divide the upper leftmost segment 236 into four Hilbert curves 220 as illustrated in FIG. 3.

It should be appreciated that for any Hilbert curve, each unique row and column location of the corresponding matrix is intersected only once without the curve intersecting itself. Comparing FIGS. 3 and 4, the area of matrix 222 and the area of matrix 232 is approximately the same, and as n increases, the amount of the area occupied by the corresponding Hilbert curve pattern appears greater. Accordingly as a common area is divided to provide matrices of increasing valves of n, the density of a corresponding Hilbert curve becomes greater, such that the square matrix is filled by the curve as n approaches infinity.

Figure 5:
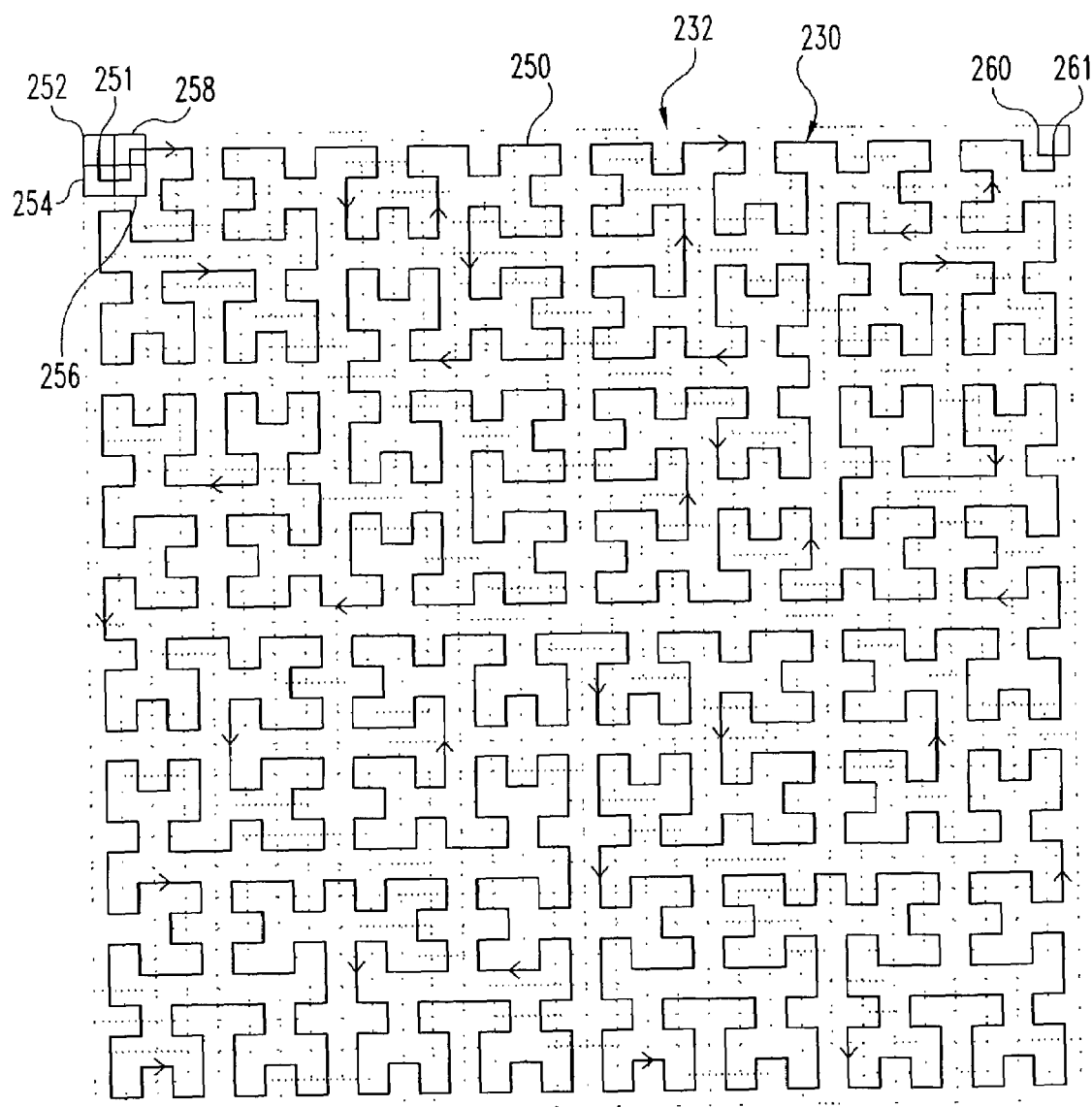

To spatially locate the image elements relative to a desired and available number of display locations for the display field of display 26a or printer 26b, a square matrix having a number of (row, column) locations greater than or equal to the number of image elements is determined. One example based on Hilbert curve 230 for n=5, is illustrated in FIG. 5. Matrix 232 of FIG. 5 uses a broken line grid pattern to depict locations except for a few that are specifically designated by reference numerals. Solid line squares are used for these specifically designated locations. Each image element is assigned a unique row and column location of matrix 232. To preserve correspondence to the nucleotide base order of the genome sequence, the spatial order of the image elements progresses along path 250 corresponding to Hilbert curve 230. The directional progression of path 250 is indicated by arrowheads along curve 230. Path 250 starts at curve end 251 in the upper leftmost matrix location 252 to which the first image element is assigned. Accordingly, location 252 represents the first nucleotide base of the genome sequence being visualized. Continuing to progress along path 250, the second image element is assigned matrix location 254 to represent the second nucleotide base of the genome sequence; the third image element is assigned matrix location 256 to represent the third nucleotide base of the genome sequence; the fourth image element is assigned matrix location 258 to represent the fourth nucleotide base of the genome sequence; and so on until all image elements are assigned. For the illustrated example, if there are 32×32=1024 image elements, then the last image element is assigned matrix location 260 at curve end 261 in the upper rightmost corner.

By following path 250, the image elements are spatially ordered in correspondence to the genome sequence being represented, with consecutive elements of the sequence being located next to one another. The spatial arrangement of image elements along path 250 can be used to fill a desired display field area without overlap, gaps, or breaks in the image. Furthermore, path 250 tends to represent consecutive elements in block regions of matrix 232, corresponding to contiguous sequence segments. While the assignment of image elements is described in a temporal as well as spatial order, it should be understood that the image elements can all be displayed simultaneously or in any temporal order desired, including that corresponding to the spatial order.

Figure 6:
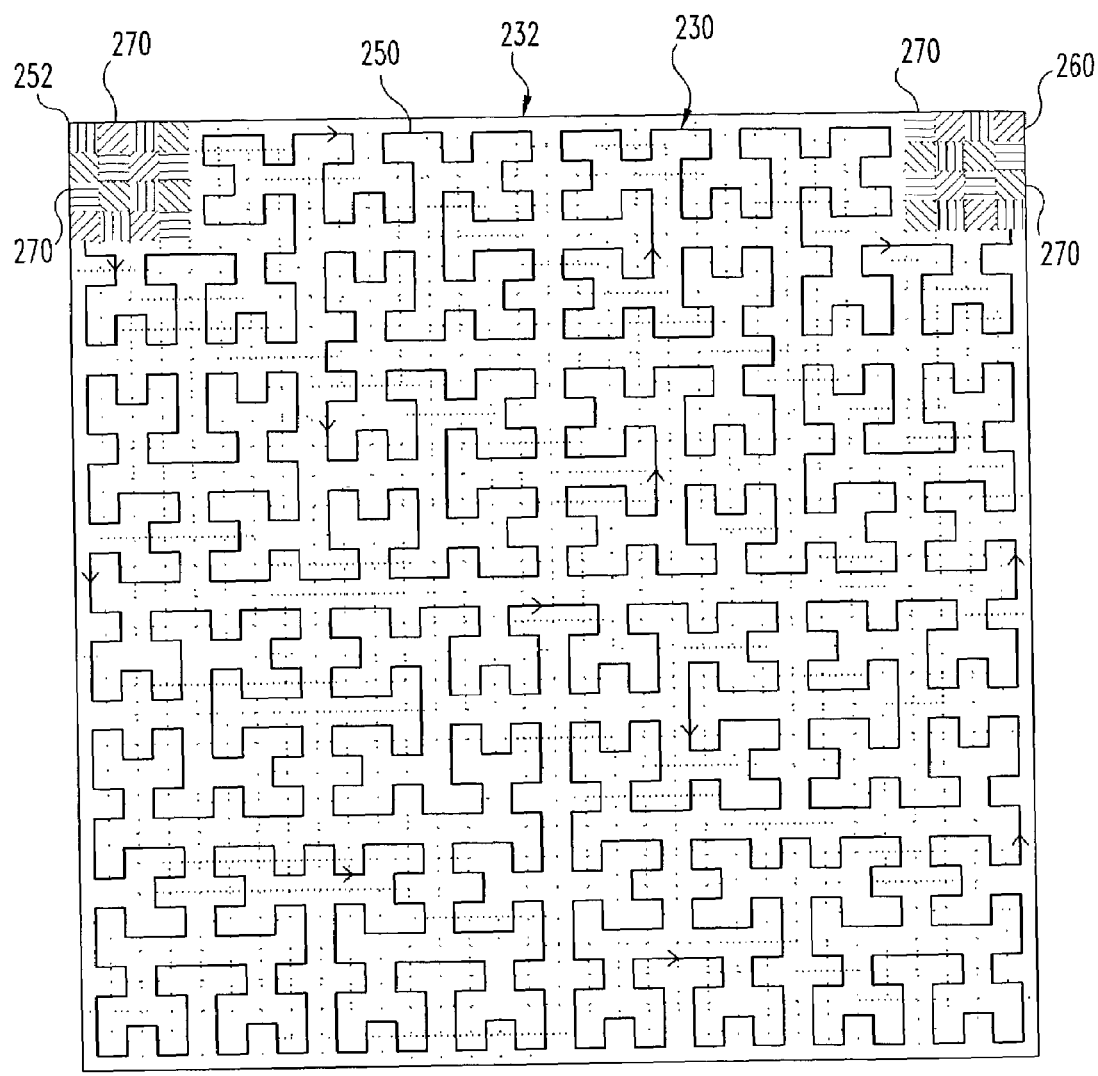
FIG. 6 is a view of different stages of progression of a spatial arrangement of image elements in accordance with the process of FIG. 2, using the Hilbert curve diagrammed in FIG. 4.

FIG. 6 provides a further illustration of the spatial ordering of the nucleotide sequence in accordance with path 250 corresponding to a Hilbert curve for n=5. In FIG. 6, the repeated nucleotide sequence ACGT is illustrated; where A is represented by a vertical parallel line pattern, C is represented by a pattern of parallel lines slanting downward from left to right, G is represented by a horizontal parallel line pattern, and T is represented by a pattern of parallel lines slanting upward from left to right. For each different nucleotide base type, the corresponding A, C, G, or T line pattern fills in the respective location of matrix 232 to visualize the repeating sequence. These line-fill patterns for the concatenated sequence "ACGTACGTACGTACGT" are only illustrated for the first sixteen and last sixteen locations of matrix 232; where the corresponding portions of curve 230 and path 250 are not shown. It should be understood that these patterns would be used in the remaining matrix locations following the course defined by path 250. Also, it should be appreciated that the matrix locations filled in this manner can each be regarded as a type of image element, with the different line-fill patterns providing different appearances representative of the different nucleotide base types. Accordingly, a representative number of the matrix locations with fill patterns are designated image elements 270. Alternatively or additionally, such appearance differentiation can be provided with varying coloration, and/or different shapes or visual patterns as would occur to those skilled in the art.

While the FIGS. 5 and 6 examples are instructive, visualizations of RNA sequences of viruses, bacteria genomes, and chromosomes would typically involve many more nucleotide bases than could be represented one-to-one with a 32 by 32 matrix of image elements. Experiments have been conducted to prepare visualizations of publicly available bacteria genome sequences with a Hilbert curve pattern in near real time on a SUN ULTRA 10 workstation with 256 megabytes (256 M) of memory. For these experiments, nine bacterial genomes were obtained from The Institute for Genomic Research at world wide web Universal Research Locator (URL) www.tigr.org. The results are represented by FIGS. 7, 10–16, and 18–21 and indicate that a genome sequence with over two million nucleotides can be processed to prepare a visualization in approximately one CPU second (or less than two wall-clock seconds) on a SUN Ultra 10 workstation with 256M of memory.

The four orthogonal directions (down, right, up, left) of the Hilbert curve are amenable to a recursive procedure. In one form, four recursion calls in these four 2D directions, i.e., left, right, up, and down are made to form a desired Hilbert curve of a desired scale. The book: *Algorithms+Data Structures=Programs* authored by N. Wirth and published by Prentice Hall, 1976 (the "Wirth Algorithm") is cited as a source of additional information concerning standard algorithms to generate Hilbert curves. Another source, *Space-Filling Curves and a Measure of Coherence in Graphics Gems*, pages 26–30 authored by D. Voorhies and published by Academic Press, 1991 provides a slightly different algorithm implementation, that could also be utilized.

Table I below more specifically lists the nine bacteria genome examples used in various experimental examples of the present application. A recursive program based on the Wirth algorithm was utilized to generate the Hilbert curve pattern. The bacteria type, the strain, the number of nucleotides in the genome, the CPU seconds, and real wall-clock seconds are indicated as follows in the first, second, third, fourth, and fifth columns of Table I, respectively:

TABLE I

| Bacteria | Strain | Size | CPU (s) | Wall Clock (s) |
|---|---|---|---|---|
| Chlamydia trachomatis | Serovar D (D/UW-3/Cx) | 1,042,519 | 0.6 | 1.1 |
| (a.k.a. C. trachomatis) | MoPn | 1,069,412 | 0.6 | 1.1 |
| Chamydophila | AR39 | 1,229,858 | 0.6 | 1.1 |
| pneumoniae | CWL029 | 1,230,230 | 0.6 | 1.1 |
| (a.k.a. C. pneumoniae) | J138 | 1,226,565 | 0.6 | 1.1 |
| Helicobacter pylori | 26695 | 1,667,876 | 0.8 | 1.3 |
| (a.k.a. H. pylori) | J99 | 1,643,831 | 0.8 | 1.3 |
| Neisseria meningitides | MC58 | 2,272,351 | 1.1 | 1.8 |
| (a.k.a. N. meningitides) | Z2491 | 2,184,406 | 1.0 | 1.8 |

Figure 7:
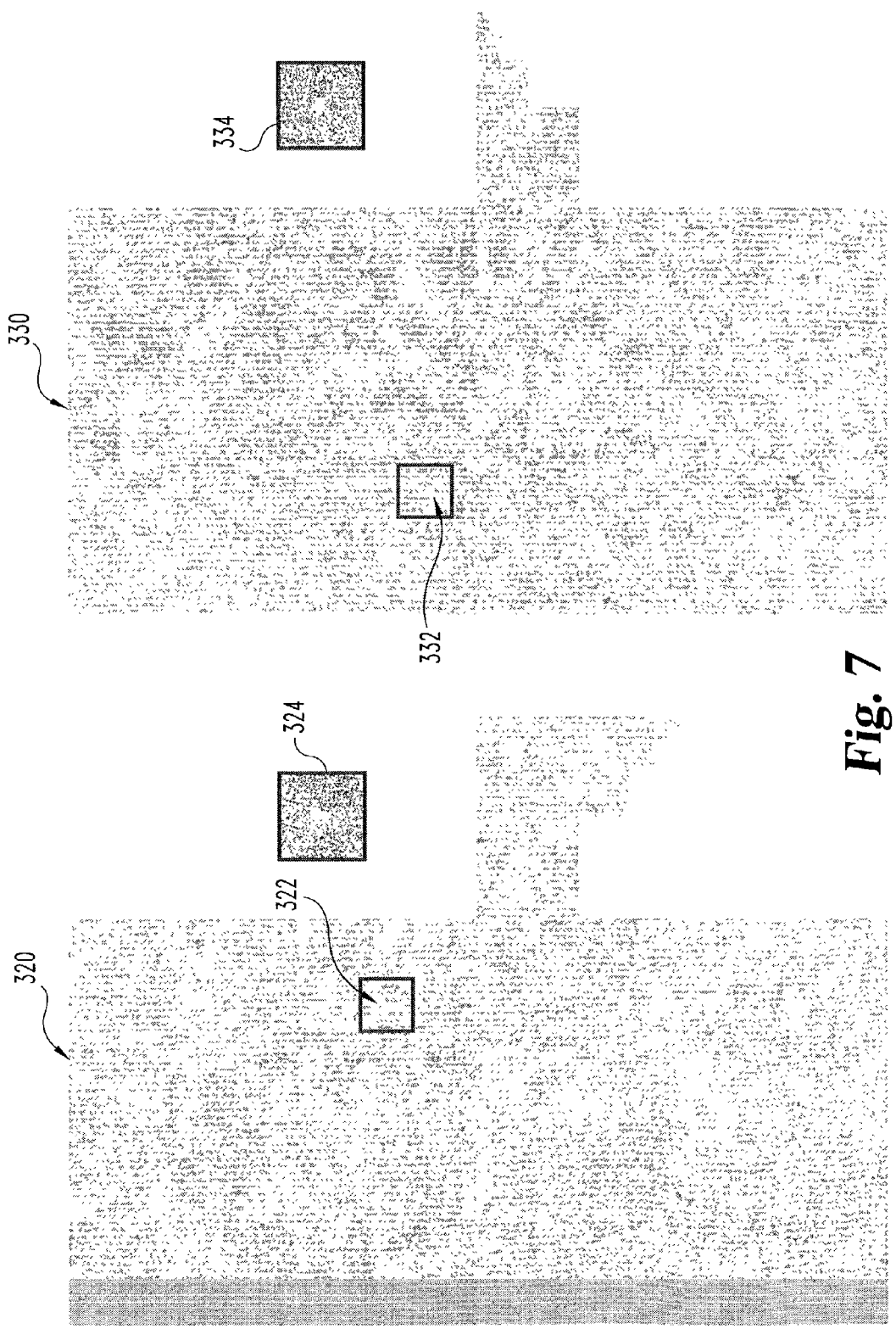
FIG. 7 is a comparative view of two computer-generated, gray scale representations of chromatically colored visualizations for two different types of bacteria genome generated in accordance with the process of FIG. 2.

FIG. 7 is a comparative view of gray scale representations of chromatically colored visualizations 320 and 330 of two different strains of *Neisseria meningitides* (MC58 and Z2491), respectively, generated with the Hilbert curve pattern in stage 126, and allocating the smallest addressable display location to each image element. For each of visualizations 320 and 330, a 2048 by 2048 pixel display area was utilized to provide the square shape for the corresponding Hilbert curve pattern. The smallest addressable location (and image element) was a pixel for this display area. Accordingly, over four million image elements could be depicted. Also, for this arrangement each visualization 320 and 330 only fills-up approximately half of the 2048×2048 display area because each has approximately 2 million nucleotides. Visualization 320 of strain MC58 occupies a larger area than visualization 330 because its genome has about 100,000 nucleotides more than that of strain Z2491 (see Table I).

To display both visualizations 320 and 330 on a common display at the same time without overlap, such display could provide at least two 2048×2048 display areas. Alternatively or additionally, the portion of the 2048×2048 display area not occupied by image elements representing one of visualizations 320 and 330 could be used for presentation of image elements of the other of visualizations 320 and 330; a scrolling or a panning operation could be utilized to view different regions of a graphic display area presenting visualizations 320 and 330, where only a portion of the two visualizations 320 and 330 collectively is visible for a given scroll or pan position; only one or a portion of one visualization 320 and 330 is displayed at a time; multiple displays are used to present the different visualizations 320 and 330; a combination of these approaches utilized; and/or a different technique is employed as would occur to one skilled in the art. Further, in addition or as an alternative to one or more graphic displays 26a, a printer 26b could be used to present one or more of the visualizations 320 and 330. Indeed, in another embodiment, display options are provided that facilitate adjustment for the number, size, and shape of the visualization areas desired.

At such a scale, the features of individual image elements in visualizations 320 and 330 are typically not readily observed by the naked eye; however, features corresponding to different groups of image elements can be observed. Visualizations 320 and 330 each include many observable square-shaped patterns with different sizes and shades. Due to the folded, self-similar block-like shapes of the Hilbert curve, these observed patterns typically correspond to different contiguous segments of the sequence being represented. Indeed, the observable features include white spot 322 of visualization 320 and white spot 332 of visualization 330. The regions about white spots 322 and 332 are each enclosed by a square solid-line image overlay, which are duplicated and enlarged in window regions 324 and 334, respectively. White spots 322 and 332 appear to be similar as confirmed by the alphabet-based representations of the corresponding genome segments listed in Tables II and III, respectively, as follows:

TABLE II

AAACAACAAACAACAAACAACAAACAACAAACAACAAACAACAAACAACA

AACAACAAACAACAAACAACAAACAACAAACAACAAACAACAAACAACAA

ACAACAAACAACAAACAACAAACAACAAACAACAAACAACAAACAACAAA

CAACAAACAACAAACAACAAACAACAAACAACAAACAACAAACAACAAAC

AACAAACAACAAACAACAAACAACAAACAACAAACAACAAAC

TABLE III

AAACAACAAACAACAAACAACAAACAACAAACAACAAACAACAAACAACA

AACAACAAACAACAAACAACAAACAACAAACAACAAACAACAAACAACAA

ACAACAAACAACAAACAACAAACAACAAACAACAAACAACAAACAACAAA

CAACAAACAACAAACAACAAACAACAAACAACAAAC

Both genome segments of Table II and Table III can be constructed by concatenating the segment "AAACAAC" repeatedly (about 34 times for MC58 and 27 times for Z2491). Because the folding of a Hilbert curve is relatively tight, it has been found that a tiny area as small as a ten thousandth of the overall size can still be readily detected by visual inspection with the naked eye. Experiments have further indicated that Table II and Table III segments are not only unique to genomes of N. meningitides, but also can be found within other bacterial genomes. Accordingly, the locations of these white spot features have been selected as a common reference point to align the N. meningitides genomes.

Figure 8:
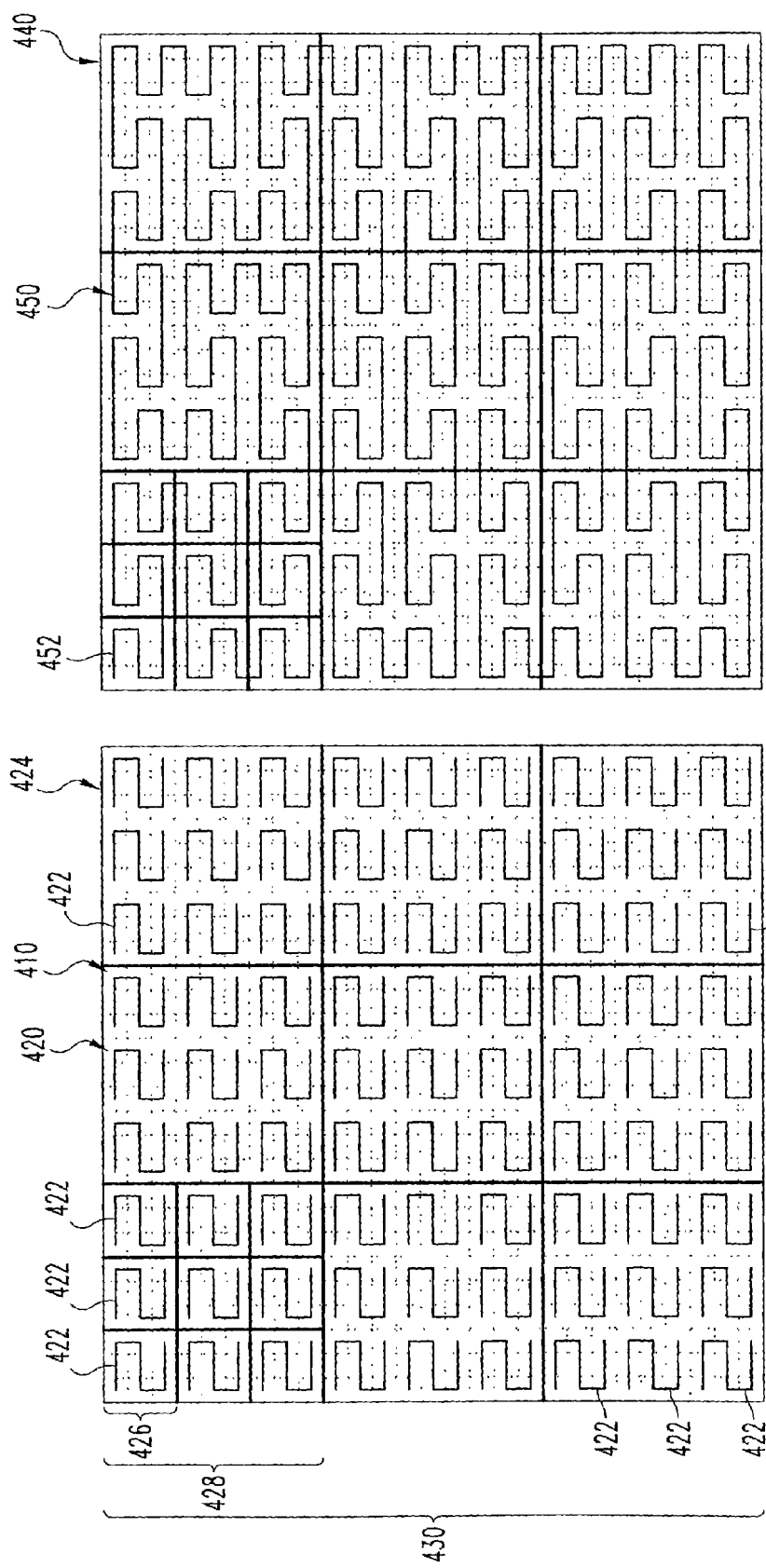
FIGS. 8 and 9 are diagrams representative of other image element patterns.

Alternatively or additionally, visualizations can be generated in accordance with the present invention by spatially arranging the image elements along a path pattern different than a Hilbert curve. In one example, the image elements are displayed across the display field in adjacent parallel lines, with the spatial order progressing from left to right and top to bottom (a standard transversal scan line pattern). Referring to FIG. 8, diagram 410 illustrates pattern 420 of another embodiment. Pattern 420 includes a number of repeating folded, solid line segments 422 relative to a square 32 by 32 matrix 424. Only a few of segments 422 are designated by reference numerals to preserve clarity. Like the repeating transversal line pattern just described, segments 422 are not connected to one another, resulting in gaps. Pattern 420 is self-similar at $3^n \times 3^n$ (n=1, 2, 3, . . . ), such that segments 422 visit all row/column locations of matrix 424 in the $3^i \times 3^i$ areas partitioned by lines during the $i^{th}$ recursion, before moving to the $(i+1)^{th}$ recursion and filling up a larger $3^{i+1} \times 3^{i+1}$ square based on the same pattern. Bracket 426 corresponds to one side of a square matrix for n=1 (a 3 by 3 submatrix); bracket 428 corresponds to one side of a square matrix for n=2 (a 9 by 9 submatrix); and bracket 430 corresponds to one side of a square matrix for n=3, which is the 27 by 27 matrix 424 depicted.

Figure 9:
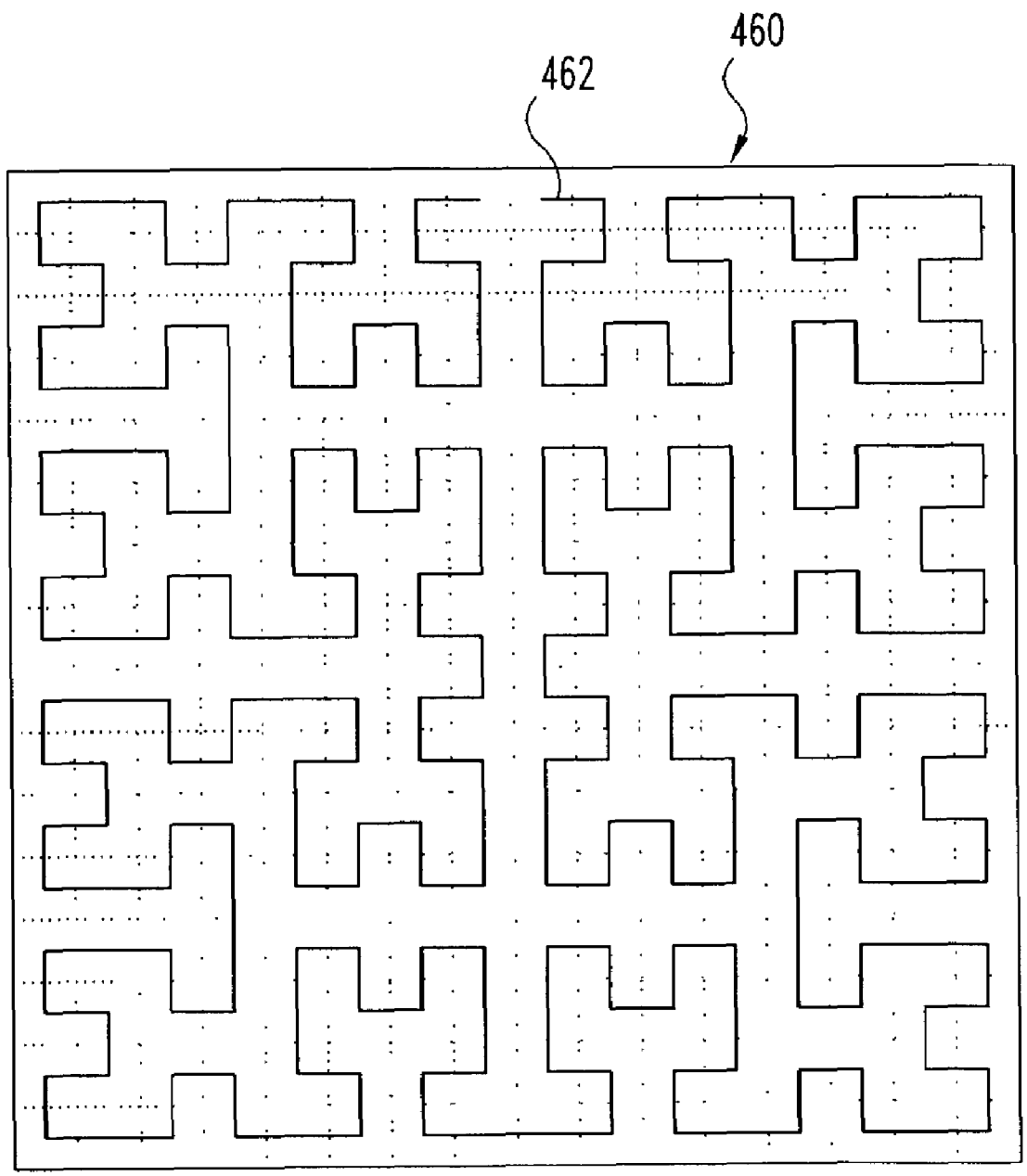

Diagram 440 of FIG. 8 illustrates a repeating, convoluted line segment pattern 450 based on another curve 452 (a "Peano-type" curve). Curve 452 is a recursive, boustrophedonic arrangement that is folded back and forth at multiple recursive levels. The pattern is self-similar at $3^n \times 3^n$ (n=1, 2, 3, . . . ) where n=3 for the example shown. FIG. 9 illustrates a repeating folded line segment pattern 460 of still another curve 462 (sometimes designated a "Moore" curve). Like the Hilbert curve, curve 462 is self-similar at $2^n \times 2^n$ (n=1, 2, 3, . . . ). In FIG. 9, curve 462 corresponds to n=4.

The Hilbert curve, Peano-type curve, and Moore curve are all fractals with a fractal dimension of two. Curves with a fractal dimension of two are sometimes designated "Peano Curves" as a class. In other words, the Hilbert Curve and Moore Curve can be considered specific examples of the Peano Curve class. As a group, members of the Peano Curve class fill a planar area of a given shape, giving rise to categorization as "space-filling," "shape-filling," or "plane-filling" curves. In the more specific case of the Hilbert curve (FIGS. 3–5), Peano-type curve (FIG. 8), and Moore curve (FIG. 9), the filled shape is a square. Other types of curves with a fractal dimension of two (Peano Curve class) include the H-fractal (filling a rectangle), Cesaro's and Polya's sweeps (filling triangle-like shapes), the snowflake sweep (filling a Koch snowflake fractal), paper-folding fractals (which are all types of sweeps), and dragon fractal, just to name a few nonlimiting examples.

It should be appreciated that fractals can be described in terms of "self-similarity" which is the property of having the same visual pattern repeated at different scales. As a consequence a fractal curve of infinite length appears equally detailed at any level of magnification, such that it is independent of scale. Said differently, a self-similar portion of an infinite fractal curve, magnified in scale, appears identical to the whole curve. This repetition of pattern can also be observed for finite approximations of such curves as in the example of the Hilbert curve illustrated in FIGS. 3 and 4. For the Hilbert curve, self-similarity at $2^n \times 2^n$ (n=1, 2, 3, . . . ) indicates that there are n2 self-similar patterns for each integer value of n. For example, in FIG. 3 four ($n^2$=4) self-similar patterns of equal size (segments 224) are depicted for n equal to two (n=2). It can also be observed that for a Hilbert Curve with a positive, nonzero integer value of n, the curve can be decomposed into self-similar patterns of n−1 each occupying a square $2^{(n-1)} \times 2^{(n-1)}$ matrix. For example, curve 230 (n=5) can be decomposed into four self-similar segments 234(n=4), which in turn can each be decomposed into four self-similar segments 236 (n =3). Likewise, segments 236 can each be decomposed into four self-similar segments 220 as illustrated in FIG. 3. It should be understood that the Moore curve (see FIG. 9) representation has the same self-similarity properties as the Hilbert curve. Accordingly, the Hilbert and Moore curves exhibit a self-similarity based on a 2 by 2 matrix.

In comparison, (patterns 420 and 450 of FIG. 8 are self-similar at $3^n \times 3^n$ (n=1, 2, 3, . . . ); where the fundamental motif corresponds to n=1. Patterns 420 and 450 thus exhibit a self-similarity based on a 3 by 3 matrix. For these examples, each pattern with a positive, nonzero integer value of n can be decomposed into self-similar patterns of n−1. Thus, patterns 420 and 440 for which n=3 can be decomposed into nine self-similar patterns of n=2, which in turn can each be decomposed into nine patterns of n=1. It should further be appreciated that while pattern 420 exhibits self-similarity, the discontinuity of segments 422 preclude it from collectively being considered a single fractal; however, each segment 422 corresponds to the fundamental fractal motif of curve 452. Also, it should be understood that while fractal curves are commonly regarded as infinite in the abstract, the present invention typically applies finite forms of such curves.

In addition to self-similarity, another fractal property relating to certain embodiments of the present invention is dimension. Topological dimension is a commonly understood concept that assigns integer dimensional values of zero to a point, one to a line (1-D), two to a plane (2-D), and three to a cube (3-D). With regard to fractals, the notion arises that a line which turns or folds to a certain degree can be described with a fractional dimension between one and two. Likewise, a convoluted surface can be dimensionally described between two and three. Indeed, all members of the Peano Curve class are a line having a topological dimension of one, but are so convoluted that they each fill a given planar area when infinite, resulting in a fractal dimension of two.

As used herein, "fractal dimension" is determined in accordance with the following equation: fractal dimension (FD)=log (SSP)/log(m); where SSP is the integer number of self-similar patterns observed for an integer magnification factor of m. In other words, fractal dimension is an exponent of the number of self-similar patterns (SSP) exhibited when applying a magnification factor of m. In the case of a Hilbert or Moore curve, for a magnification factor of two (m=2), there are four self-similar patterns (SSP=4=$m^2$). The resulting exponent is two (FD=2). For the finite examples of FIGS. 3 and 4 a magnification factor of two (m=2) results when going from a $2^n \times 2^n$ matrix to a $2^{(n+1)} \times 2^{(n+1)}$ matrix. For the curve 452 of FIG. 8, a magnification factor of three (m=3) results when going from a $3^n \times 3^n$ matrix to a $3^{(n+1)} + 3^{(n+1)}$ matrix. For all these cases, FD=(log (SSP)/log(m))= log(m)2/log(m)=2(log(m)/log(m))=2.

In a most preferred embodiment of the present invention, image elements are spatially arranged in a pattern corresponding to a Hilbert or Moore curve. In more preferred embodiments, image elements are spatially arranged in a pattern corresponding to a curve with a fractal dimension of at least 2, a shape-filling curve, and/or one or more curve types belonging to the Peano Curve class. In preferred embodiments, image elements are otherwise spatially arranged in correspondence to a transverse line pattern previously described, a repeating pattern of broken lines (such as diagram 410 of FIG. 8), one or more nonfractal curves, and/or a different pattern as would occur to one skilled in the art. Indeed, in one preferred form of the present invention, stage 126 includes the option of selecting among different spatial patterns for the image elements, including those described herein and/or others as would occur to one skilled in the art.

Returning to FIG. 2, routine 120 proceeds from stage 126 to stage 128 to perform Gaussian filtering or smoothing of the resulting visualization image. A Gaussian filter is a 2-D convolution operator that is used to blur pixel-based digital images and remove noise. It can use a circularly symmetric kernel that has the form of the following equation (1)

$$G(x, y) = \frac{1}{2\pi\sigma^2} e^{-\left(\frac{x^2+y^2}{2\sigma^2}\right)}$$

where σ is the standard deviation of the distribution, and x and y are cartesian coordinates that map the image area. The convolution can be performed with relative speed because equation (1) for the 2-D isotropic Gaussian shown above is separable into x and y components. Thus, the 2-D convolution can be computed effectively by first convolving with a 1-D Gaussian in the x direction, and then convolving with a 1-D Gaussian in the y direction.

Figure 10:
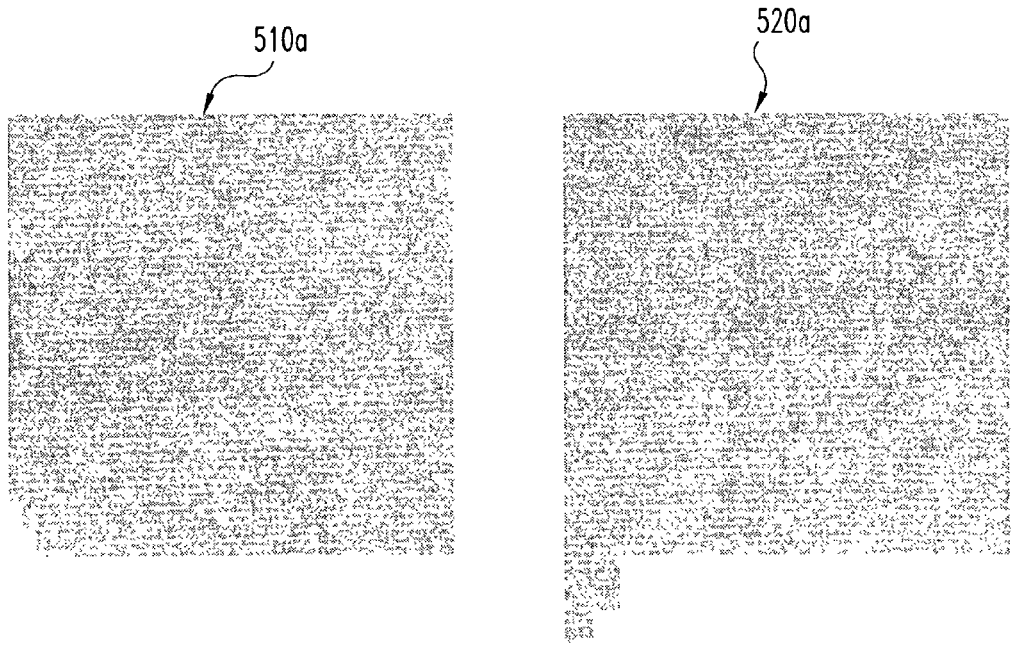
FIG. 10 is a comparative view of two computer-generated, gray scale representations of chromatically colored visualizations for two other types of bacteria genome generated in accordance with the process of FIG. 2.

Referring to FIG. 10, two different strains of Chlamydia trachomatis (Serovar D and MoPn) are depicted as visualizations 510*a* and 520*a*, respectively, after spatial arrangement in a pattern corresponding to a Hilbert curve as previously described in connection with stage 126. The gray scale shading of visualizations 510*a* and 520*a* generally correspond to an overall visual impression of a grainy mixture of tan and orange-brown colors with a few significantly lighter or darker spots discernable.

Figure 11:
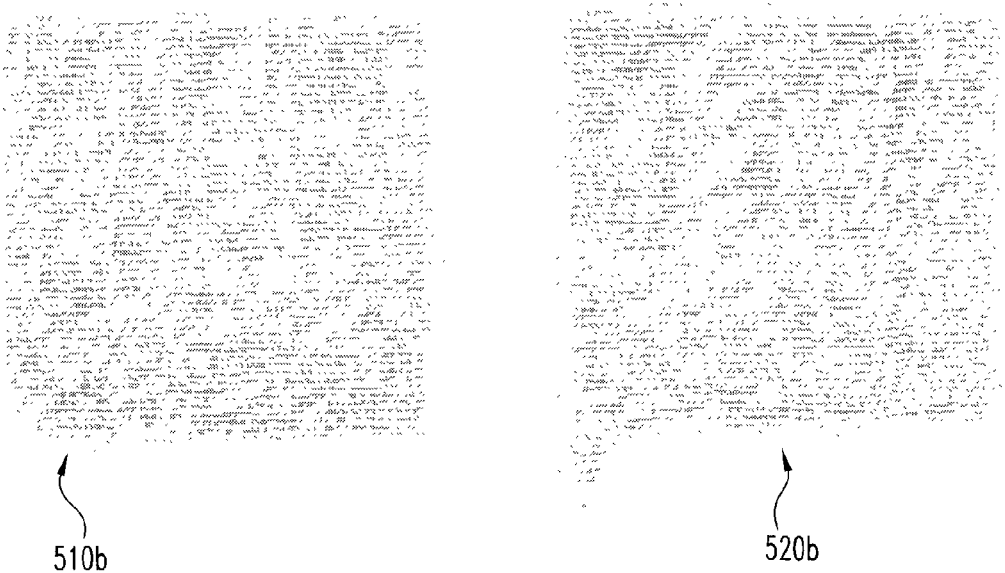
FIG. 11 is a comparative view of two computer-generated, gray scale representations of chromatically colored visualizations for the two bacteria genomes of FIG. 10 after image filtering.

Referring to FIG. 11, visualizations 510*a* and 520*a* are subjected to filtering in accordance with stage 128 to provide corresponding filtered visualizations 510*b* and 520*b* for the Serovar D and MoPn strains of C. trachomatis. Compared to visualizations 510*a* and 520*a*, visualizations 510*b* and 520*b* appear less grainy with the gray scale shading corresponding to generally the same chromatic colors. Filtered visualizations 510*b* and 520*b* resulted from convolving the corresponding datasets with a Gaussian filter using a mask radius of 36 image elements, which were pixels in this case. The mask radius is typically two standard deviations of the Gaussian curve, and is applied by two successive one dimensional convolutions in the horizontal and vertical directions. In other embodiments, highpass filtering, notch filtering, bandpass filtering, median filtering, and/or a different type of filtering may alternatively or additionally be utilized; or filtering may be absent.

Frequently, filtering is utilized to remove data that tends to obscure an informative pattern or trend. Because the filtered visualization is based on less data, a smaller displayable size in terms of dimension or scale, and/or the number of representative image elements can typically be used, while still visualizing information of interest. By way of nonlimiting example, the Gaussian filter tends to reduce the high-frequency content of the visualization and correspondingly can be represented with a lower image element resolution after such filtering. Through common filtering and rescaling/resizing in this manner, simultaneous viewing of two or more visualizations each representing genomes of a million nucleotides bases or more can be shown on a standard form of display 26*a*.

Figure 12:
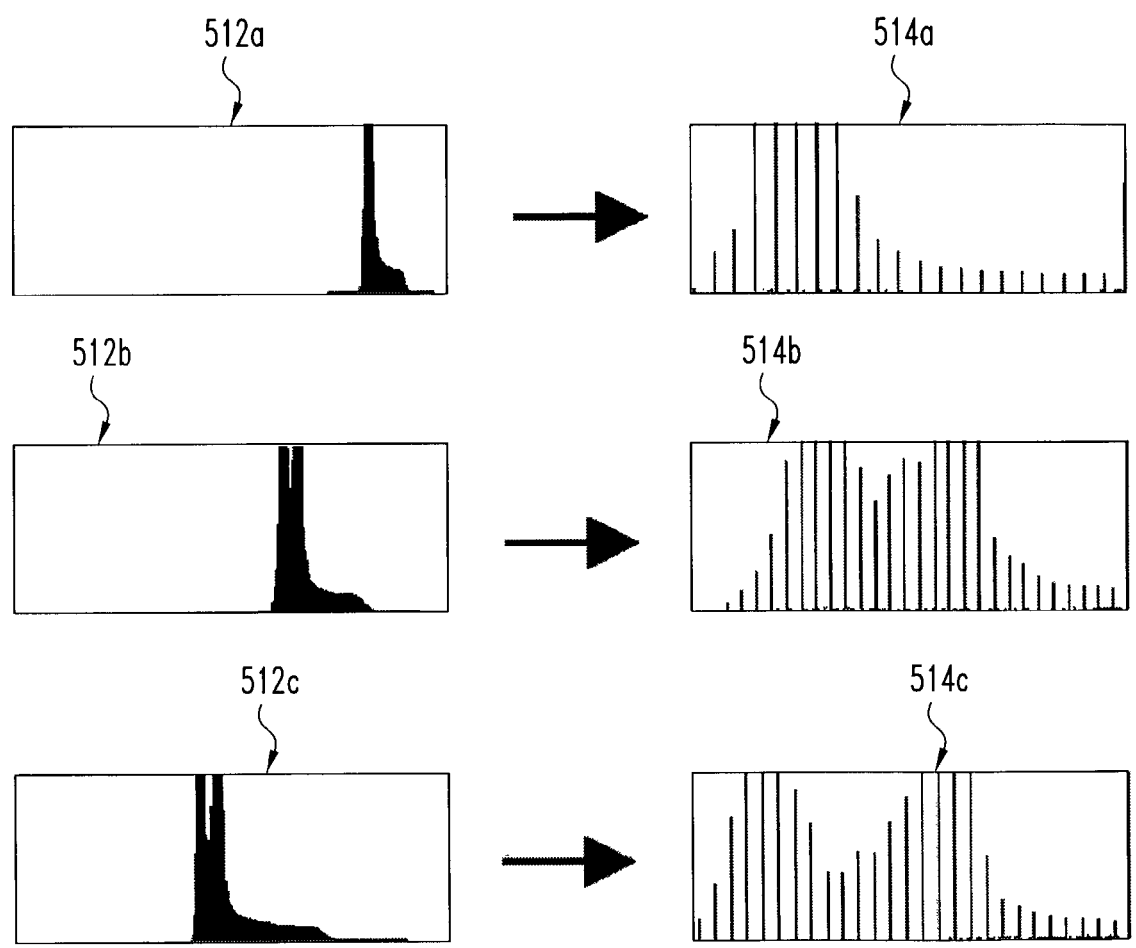
FIG. 12 is a comparative view of six histogram graphs for red, green, and blue color components of one of the visualizations shown in FIG. 11 before and after equalization.

To better visualize features of interest within the filtered visualizations 510*b* and 520*b*, adjustments to one or more color parameters can be performed in stage 130. One procedure to adjust coloration is through histogram equalization. This procedure is based on a histogram relationship that shows the number of image pixels for each of a number of different intensities. For a Red-Green-Blue (RGB) based color image, separate histogram relationships are established for each of the three red, green, and blue color components; where pixel coloration is a vector of three numbers. Referring to FIG. 12, histogram graphs 512*a*, 512*b*, and 512*c* are shown for the red, green, and blue color components of visualization 510*b* for the C. trachomatis strain Serovar D, respectively. For each graph 512*a*, 512*b*, and 512*c*; the vertical axis indicates the relative number of pixels and the horizontal axis represents the available range of intensities. The number of pixels having a given intensity value is proportional to the length of the vertical line segment that extends from the horizontal axis at such intensity value. It should be appreciated that the pixels tend to cluster in a relatively narrow portion of the available intensity range in graphs 512*a*, 512*b*, and 512*c*.

The pixel color components are equalized with respect to the available intensity range by spreading the vertical lines for each intensity over the available range. This procedure can include determining a uniform interval between adjacent peaks of graphs 512*a*, 512*b*, and 512*c* that places the rightmost and leftmost vertical pixel peaks at the rightmost and leftmost extremes of the available range. Histogram graphs 514*a*, 514*b*, and 514*c* illustrate an equalized allocation of pixels for red, green, and blue color components relative to graphs 512*a*, 512*b*, and 512*c*, respectively. Equalizing a histogram allows the pixel near the two (very low and very high) ends to have minimum and maximum displayable values.

Figure 13:
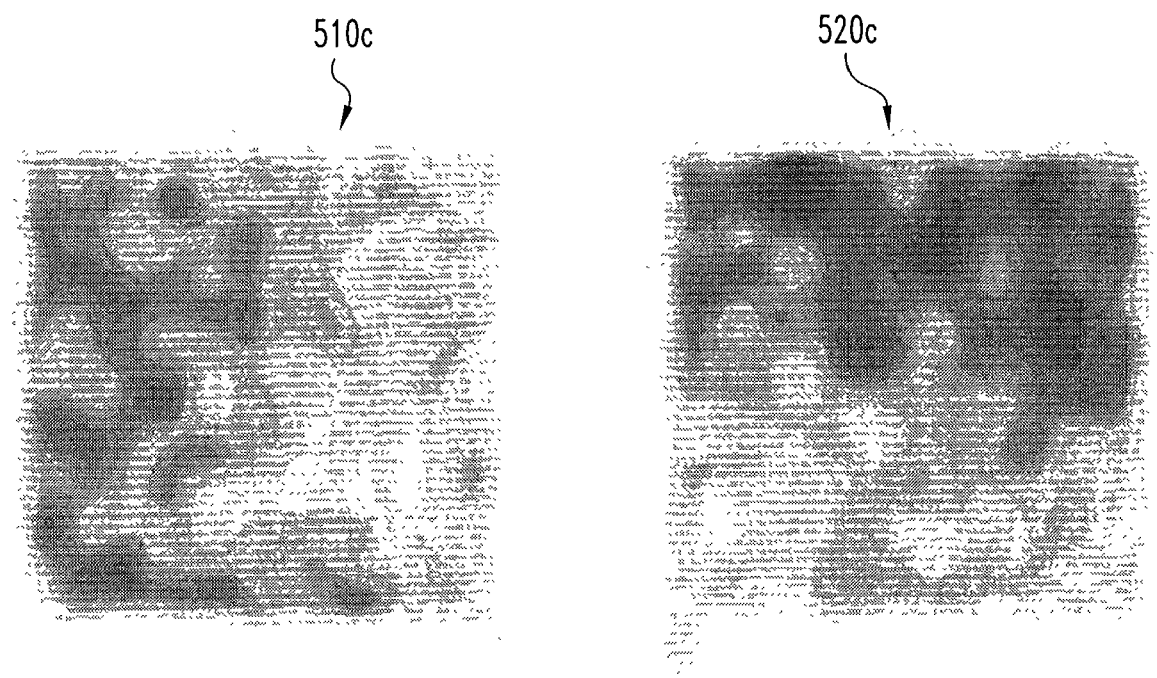
FIG. 13 is a comparative view of two computer-generated, gray scale representations of chromatically colored visualizations obtained by histogram equalization of a red color component of the visualizations of FIG. 11.
Figure 14:
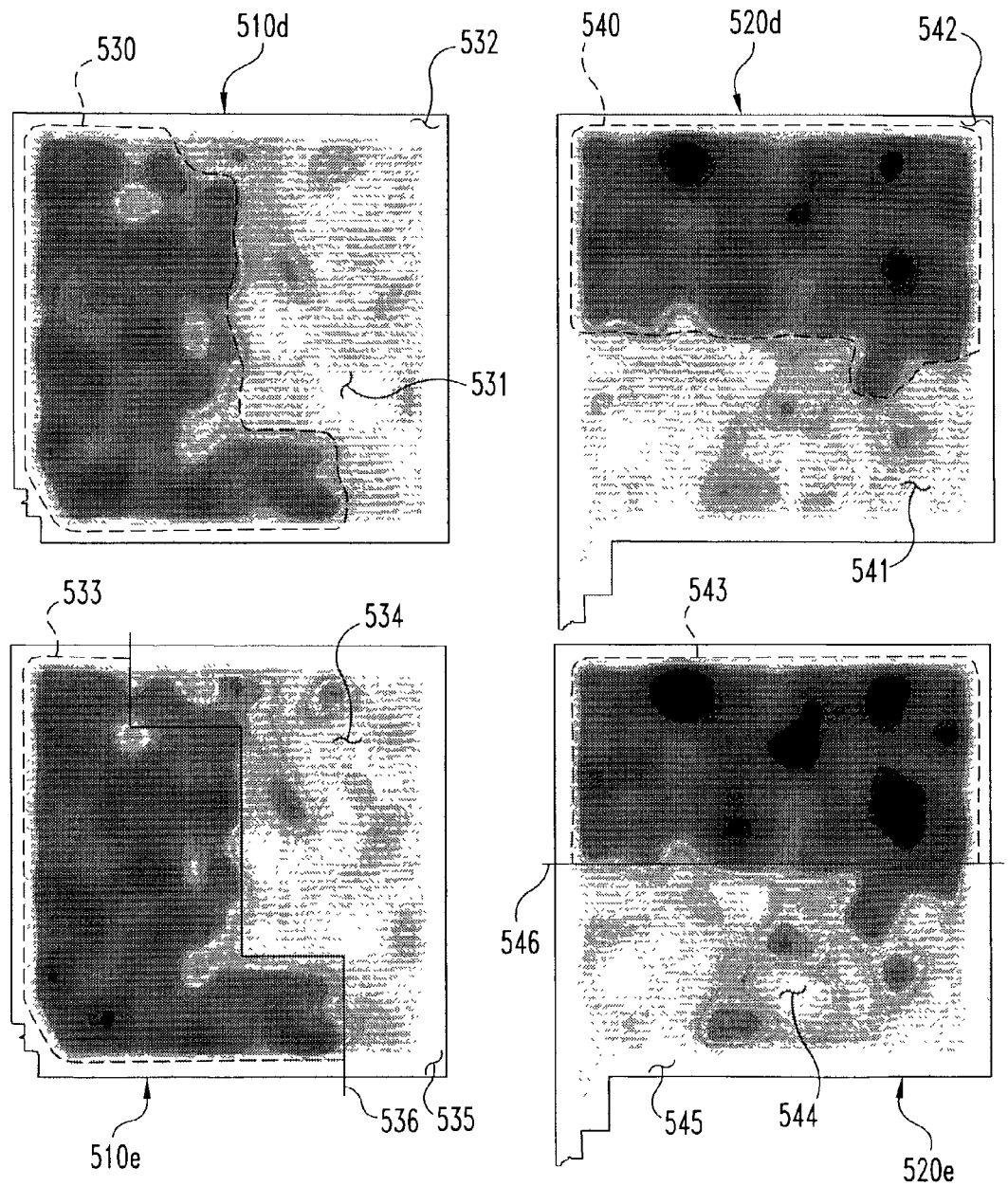
FIG. 14 is a comparative view of four computer-generated, gray scale representations of chromatically colored visualizations obtained by successive histogram equalization of a green color component and then a blue color component of the visualizations FIG. 13.
Figure 15:
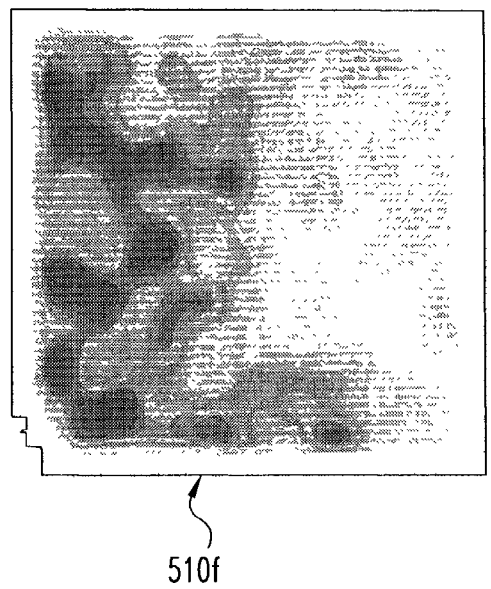
FIG. 15 is a comparative view of two computer-generated, gray scale representations of chromatically colored visualizations after applying contrast stretching to two of the visualizations of FIG. 14.
Figure 15:
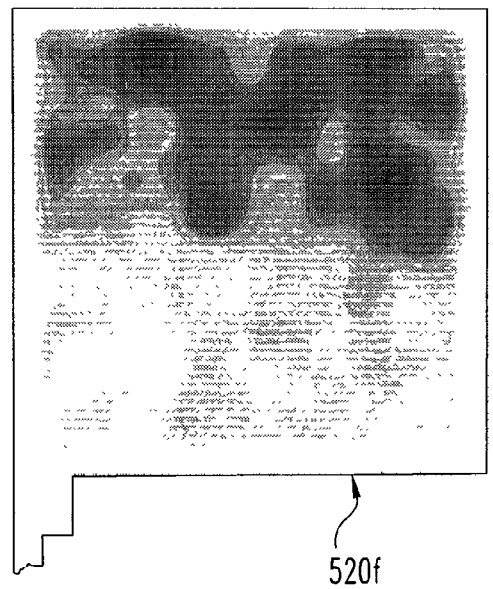

FIG. 13 shows visualizations 510*c* and 520*c* corresponding to histogram equalization of the red color component of visualizations 510*b* and 520*b* for the Serovar D and MoPn bacteria strains of C. trachomatis, respectively. In visualizations 510*c* and 520*c*, the darker gray shading approximately corresponds to a green coloration of most of the image from the center outward and the lighter shading corresponds to salmon and tan coloration, which is most prevalent near the image borders. The prominent emergence of green coloration results from the shift in range of the red color component through histogram equalization.

FIG. 14 shows visualizations 510*d* and 520*d* after histogram equalization of the green color component of visualizations 510*c* and 520*c*, respectively. The darker gray-scale shading of region 530 for visualization 510*d* and region 540 for visualization 520*d* represent a mottled brown coloration. Regions 530 and 540 have each been generally outlined with a broken line pattern. The intermediate gray-scale shading of region 531 for visualization 510*d* and region 541 for visualization 520*d* represent a mottled green coloration. Border region 532 of visualization 510*d* and border region 542 of visualization 520*d* represent a predominately yellow coloration.

Also shown in FIG. 14 are visualizations 510*e* and 520*e* after histogram equalization of the blue color component of visualizations 510*d* and 520*d*, respectively. The darker gray-scale shading of region 533 of visualization 510*e* and region 543 of visualization 520*e* represents a mottled brown coloration that is generally darker in appearance than corresponding regions 530 and 540 of visualizations 510*d* and 520*d*. Regions 533 and 543 are partially outlined with a broken line pattern to enhance clarity. The intermediate gray-scale shading of region 534 for visualization 510*e* and region 544 for visualization 520*e* represents a mottled blue coloration. Border region 535 of visualization 510*e* and border region 545 of visualization 520*e* are each representative of a predominately white coloration. It should be appreciated that the successive color component equalizations of the FIGS. 13 and 14 examples can progressively bring-out further structural features of the corresponding visualizations.

As revealed in visualizations 510*d*, 510*e*, 520*d*, and 520*e*a structural pattern emerges when comparing regions 530 and 531, regions 533 and 534, regions 540 and 541, and regions 543 and 544. Region borderline 536 is shown in visualization 510*e* to further indicate the separate regions 533 and 534, and region borderline 546 is shown in visualization 520*e* to further indicate the separate regions 543 and 544. It was discovered that regions 533 and 534 represent two contiguous sequence segments of the Serovar D strain, and regions 543 and 544 represent two contiguous sequence segments of the MoPn strain. The connection point between such contiguous segments can be desirable as an alignment reference point for genome comparison, which is further described hereinafter.

Another color component that can be adjusted during stage 130 is image contrast. Contrast stretching increases the initial contrast values of the pixels to cover a desired range of values. It applies a linear scaling function to the pixel values. As a result, the enhancement can be less dramatic than histogram equalization, and in some situations can reduce visualization blurring. FIG. 15 shows visualizations 510*f* and 520*f* that result from contrast stretching visualizations 510*e* and 520*e*, respectively, with wider spectrums of both brown and blue colors.

As an addition or alternative to the RGB color model; the Intensity-Hue-Saturation (IHS) model can be used to characterize a color in terms of its intensity (brightness), hue (average wavelength), and saturation (the amount of white in the color). Under appropriate conditions, it is sometimes easier to directly derive the overall intensity and color of perceived light of all pixels using the IHS color space. For example, increasing the saturation values represents a move across the color wheel towards the white center. FIG. 16 shows visualizations 510*g* and 520*g* after saturation adjustment of visualizations 510*e* and 520*e*, respectively. Although not as readily illustrated in a gray-scale representation, visualizations 510*g* and 520*g* appear to have richer and more intensified color contents than visualizations 510*f* and 520*f* of FIG. 15 for this example. For the production of visualizations shown in FIGS. 11, 13, 14, and 15 in accordance with stages 128 and 130, equipment 21 was in the form of a personal computer having 256 M of memory and a Pentium III 600 Megahertz processor (MHz) supplied by Intel Corporation. In contrast, for the production of the visualizations in FIG. 10 in accordance with stages 122, 124, and 126, equipment 21 was in the form of a Sun Ultra 10 workstation with 256 M of memory. Naturally, in other examples, different equipment 21 could be utilized to perform one or more of these stages.

The image enhancement procedures of stage 130 can be provided as separate options for selection by an operator. Alternatively or additionally, other image enhancement procedures, such as brightness adjustment, interchanging different hues, color-based masking, and/or such different procedures as would occur to one skilled in the art can be used. In still other embodiments, image enhancement in stage 130 is absent.

Referring back to FIG. 2, routine 120 proceeds from stage 130 to conditional 132 to test whether to realign a visualization. Realignment can be desirable for visual comparisons of "closed loop" bacteria genomes or in the comparison of other segments. If a realignment of one or more of the visualizations is desired, routine 120 continues from the affirmative branch of conditional 132 to stage 134 to perform the alignment. Otherwise, routine 120 proceeds from the negative branch of conditional 132 to conditional 136. Referring to FIG. 16, visualization 510*g* of the *C. trachomatis* strain Serovar D genome includes differently colored regions 530*g* and 531*g* approximately separated by borderline 536*g*, and visualization 520*g* of the *C. trachomatis* strain MoPn genome includes differently colored regions 540*g* and 541*g* approximately separated at borderline 546*g*. Regions 530*g* and 540*g* are partially outlined with a broken line pattern to enhance clarity. Regions 530*g* and 540*g* have generally the same coloration (a mottled brown) and regions 531*g* and 541*g* have generally the same coloration (a mottled blue). Borderline 536*g* generally follows a stepwise contour of a Hilbert curve segment, and borderline 546*g* is generally straight. The shape of borderlines 536*g* and 546*g* are each of the type expected to separate contiguous segments of a Hilbert curve, and correspondingly, contiguous segments of the sequence represented by image elements spatially arranged according to a Hilbert curve pattern. One realignment approach is directed to achieving similarly shaped and/or positioned borderlines 536*g* and 546*g*.

Figure 17:
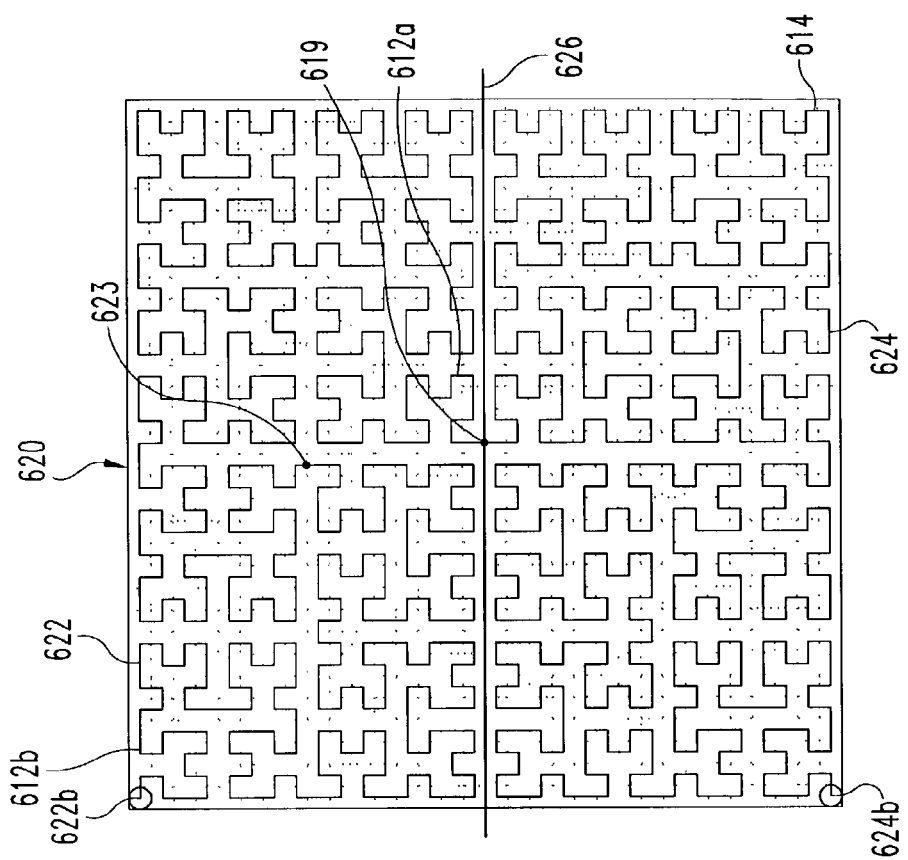
FIG. 17 is a view of two diagrams instructive in the realignment of sequences with the process of FIG. 2.
Figure 17:
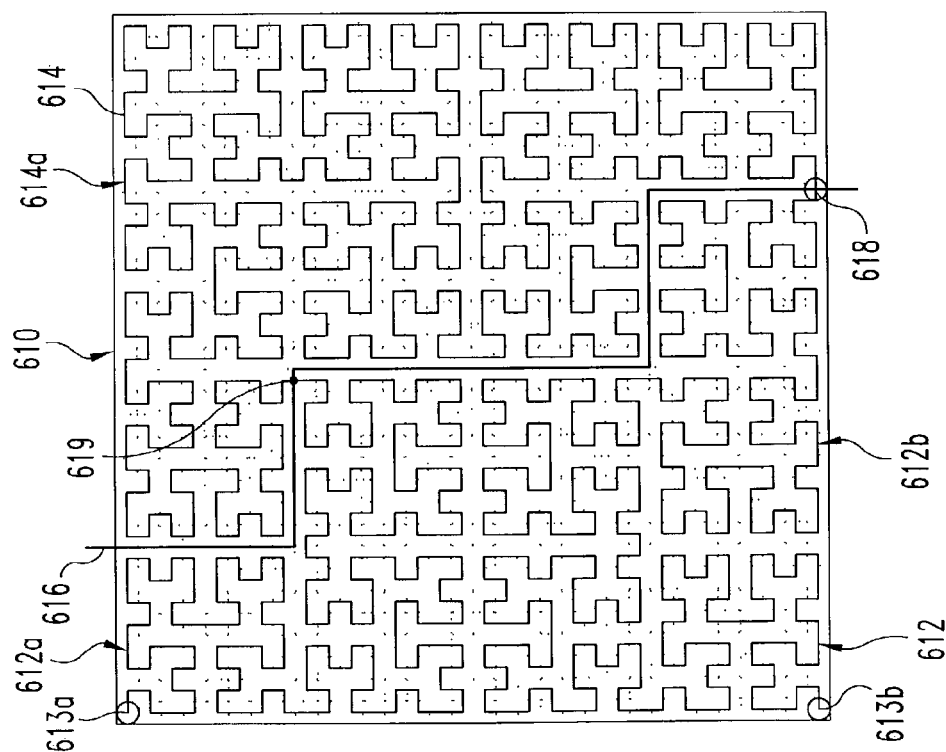

For the purpose of demonstrating one embodiment of a realignment process of the present invention, FIG. 17 symbolically represents the Serovar D strain visualization 510*g* in terms of a Hilbert curve of n =5. It should be understood that this relatively low value for n was selected to enhance understanding, and that typically n would be much greater when realigning a genome. Referring to diagram 610, different curve regions 612 and 614 are indicated corresponding to regions 530*g* and 531*g* of visualization 510*g*. Regions 612 and 614 are separated by borderline 616. Furthermore, region 612 corresponds to two separated Hilbert curve segments 612*a* and 612*b*, and region 614 corresponds to a single Hilbert curve segment 614*a*. Each of segments 612*a* and 612*b* has corresponding unconnected ends 613*a* and 613*b*. A hollow circle has been added to each end 613*a* and 613*b* to enhance clarity.

To perform the realignment, reference point 618 (indicated by hollow circle) is selected and the Servovar D sequence is shifted to more closely correspond to the pattern of visualization of 520*g* as represented in diagram 620. This shifting includes connecting segments 612*a* and 612*b* at ends 613*a* and 613*b* to provide joining point 623 represented by a solid circle; and separating ("breaking") segment 612*b* from segment 614 at reference point 618. As a result, segments 612*a*, 612*b*, and 614 are reconfigured to be connected only at joining point 623 and connection point 619 each represented with a solid dot. Remapping this reconfigured segment in correspondence to the Hilbert curve as explained in connection with stage 126, the connection of ends 613*a* and 613*b*, and separation at reference point 618 collectively operate to shift the starting point of the segment with respect to the visualization. Diagram 620 symbolically depicts the sequence after shifting, in which regions 622 and 624 correspond to regions 612 and 614. More specifically, region 622 corresponds to segments 612*a* and 612*b* after joining and shifting, and region 624 corresponds to segment 614 after separation from segment 612*b* and shifting. Regions 622 and 624 are separated by borderline 626. The break at reference point 618 provides ends 622*b* and 624*b* in the upper leftmost and lower leftmost corners of diagram 620, respectively, which are highlighted with hollow circles. Connection point 619 is shifted in diagram 620 to become the crossover point on borderline 626 between segments 612*a* and segment 614.

Figure 16:
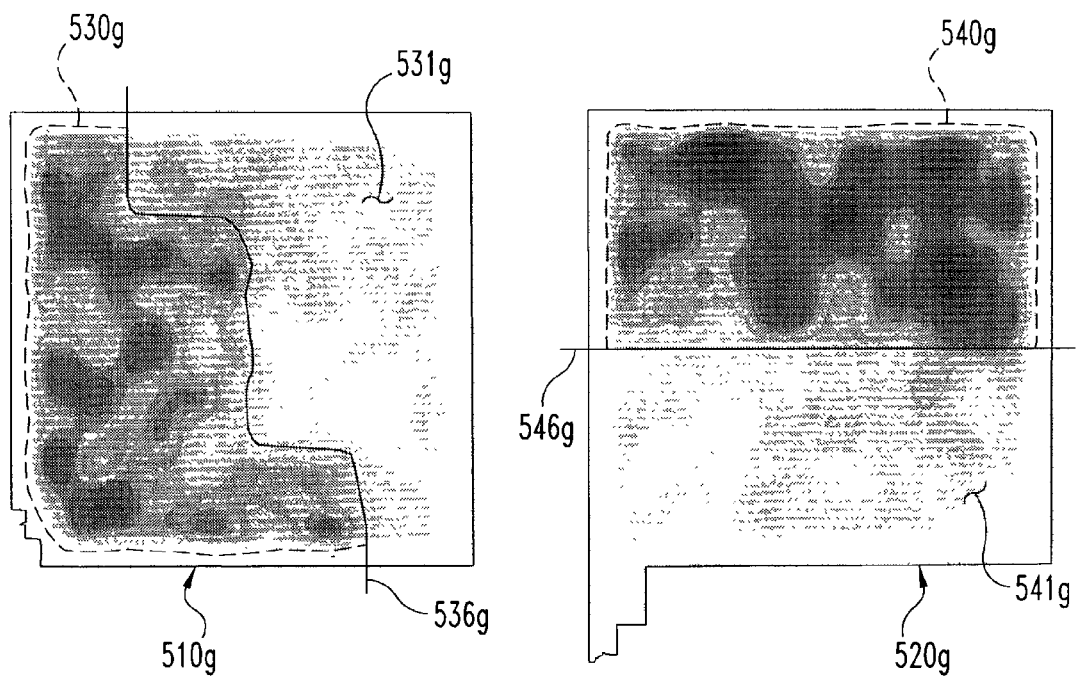
FIG. 16 is a comparative view of two computer-generated, gray scale representations of chromatically colored visualizations after adjusting saturation of two of the visualizations of FIG. 14.
Figure 18:
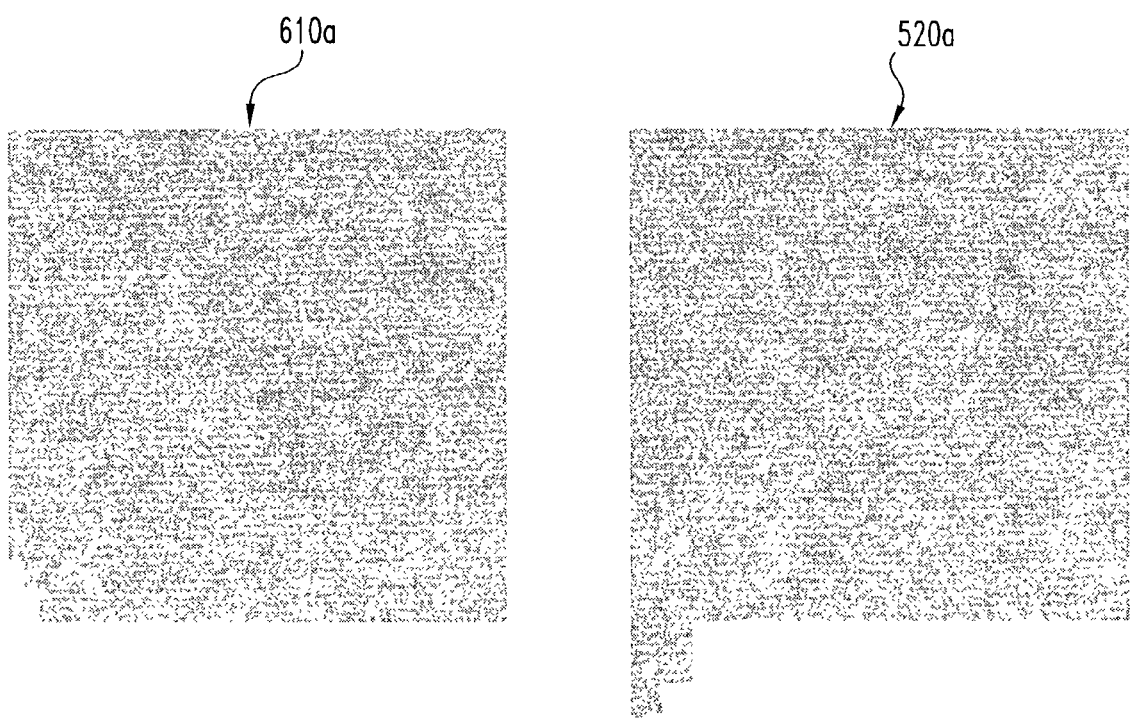
FIG. 18 is a comparative view of two computer-generated, gray scale representations of chromatically colored visualizations for the bacteria genomes shown in FIG. 10 after realignment according to the process of FIG. 2.

The enhanced visualizations 530*g* and 540*g* of FIG. 16 have been found to be advantageous in locating a desired reference point for realignment. Typically, it is desirable to perform the realignment process on the Hilbert-curve patterned data from stage 126 before any enhancements of stages 128 and/or 130 are performed. However, it is also often desired to identify the relative location of a reference point for realignment of the unenhanced visualization from the post-enhancement version of the visualization, taking into account any changes in scale or size that may have taken place before or during stages 128 and/or 130. Accordingly, FIG. 18 provides a gray-scale representation of a chromatically colored visualization 610*a* of the Servovar D sequence after realignment processing relative to the MoPn sequence, without the image enhancements described in connection with stages 128 and 130. This realignment was performed as described in connection with FIG. 17. FIG. 18 also illustrates the unenhanced visualization 520*a* of the MoPn sequence for comparison.

Figure 19:
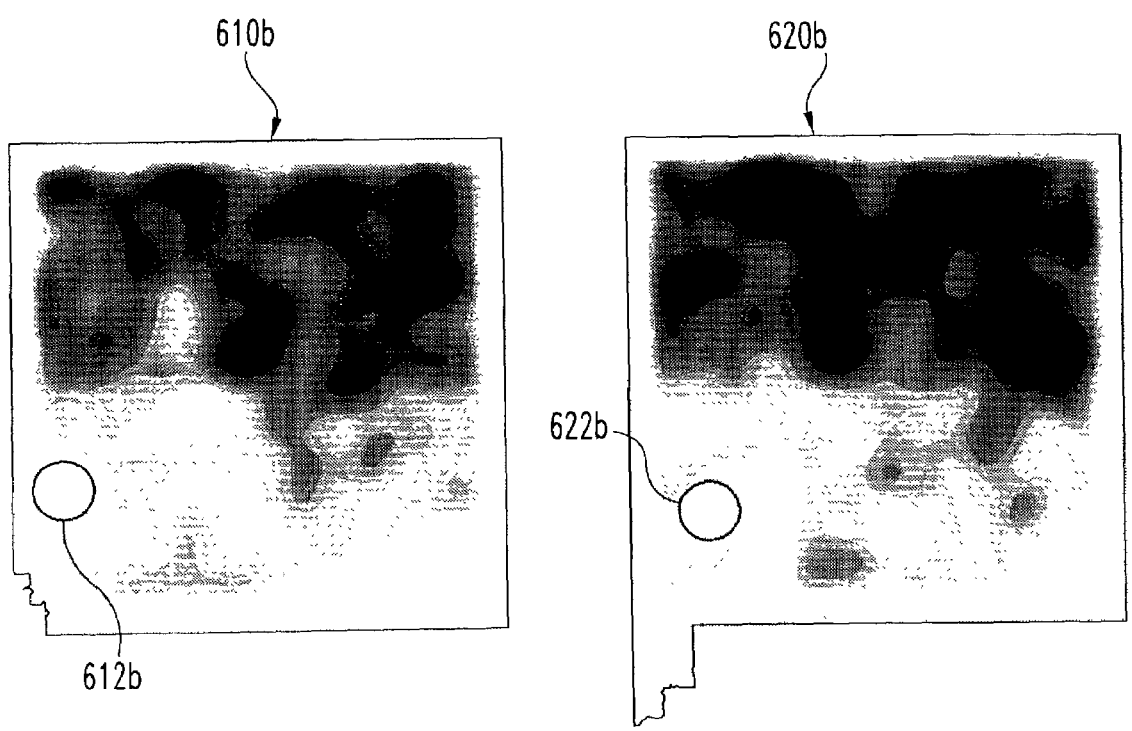
FIG. 19 is a comparative view of two computer-generated, gray scale representations of chromatically colored visualizations resulting from further processing of the visualizations of FIG. 18 in accordance with the process of FIG. 2.

FIG. 19 provides gray-scale representations of visualizations 610*b* and 620*b* corresponding to visualizations 610*a* and 520*a* of FIG. 18, respectively, after performance of various image enhancements according to stages 128 and 130. It has been found that that visualizations of this kind are typically more effective for studying similarities among multiple genomes than the voluminous printouts generated by traditional automated alignment programs. For the illustrated example, visualizations 610*b* and 620*b* each include a distinctive "white-spot" area 612*b* and 622*b*, respectively. Open circles outlining each area 612*b* and 622*b* have been added to aid in the comparison.

Partial sequence segments from areas 612*b* and 622*b* were extracted (about 4000 nucleotides each) and the ClustalW program of the MacVector v7.0 package was applied to these segments to perform a computational-based alignment study. The results of this study show that the two segments are about 80% identical, as compared to an overall similarity between the two whole genomes of about 73%; and thus confirm areas 612*b* and 622*b* correspond to homologous regions. It should be appreciated that in addition to the visual detection of areas 612*b* and 622*b* as homologous regions, visualizations 610*b* and 620*b* provide alignment information of entire bacteria genomes with millions of nucleotides with much less complexity than typical reports of traditional programs that analyze only a few thousand nucleotides.

In one embodiment of the present invention, visualizations according to routine 120 are compared with the naked eye, resulting in the identification of similar sequence segments for different genomes. For this particular embodiment, these segments preferably have a percent identity of at least 70% as determined by comparing sequence information with the MacVector computer program, version 7.0, available from Oxford Molecular Group, Inc. (Beaverton, Oreg.). The MacVector program defines identity as the number of identical aligned symbols (i.e., nucleotides or amino acids), divided by the total number of symbols in the shorter of the two sequence segments being analyzed. Parameters for a percent identity determination of nucleotide sequences with the MacVector program include: (1) for pairwise alignment parameters: (a) Ktuple=1, (b) Gap penalty=1, (c) Window size=4; and (2) for multiple alignment parameters: (a) Open gap penalty=10, (b) Extended gap penalty=5, (c) Delay divergent=40%, and (d) transitions=weighted. In another embodiment relating to identity, proteins are compared and visually identified that preferably have a percent identity of at least 70% as determined with the previously described MacVector program. Parameters for a percent identity determination of such proteins with the MacVector program include: (1) for pairwise alignment: (a) matrix=BLOSUM30, (a) Alignment speed—fast, (a) Ktuple=1, (a) Gap penalty=1, Top diagonals=5, Window size=5; (2) for multiple alignment: (a) matrix BLOSUM series, (b) open gap penalty=10; (c) extended gap penalty=0.1, (d) delay divergent=40%; and (3) protein gap parameters: (a) Gap separation distance=8, (b) residue-specific penalties=yes or on, and hydrophilic residues=GPSNDQEKR.

Figure 20:
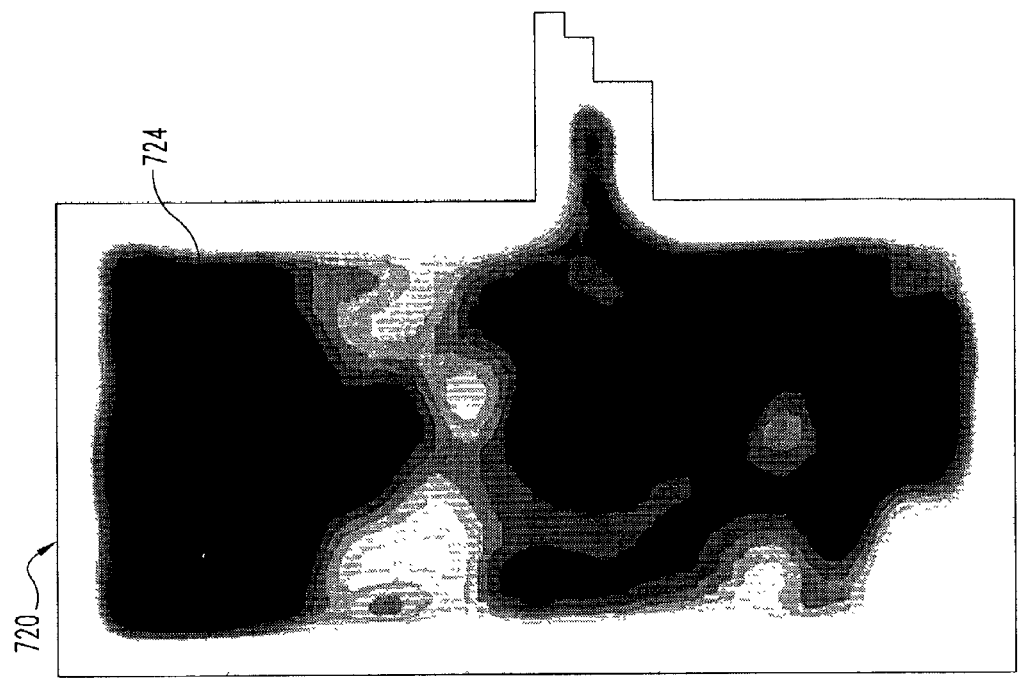
FIG. 20 is a comparative view of two computer-generated, gray scale representations of chromatically colored visualizations for still two other bacteria genomes generated with the process of FIG. 2.
Figure 20:
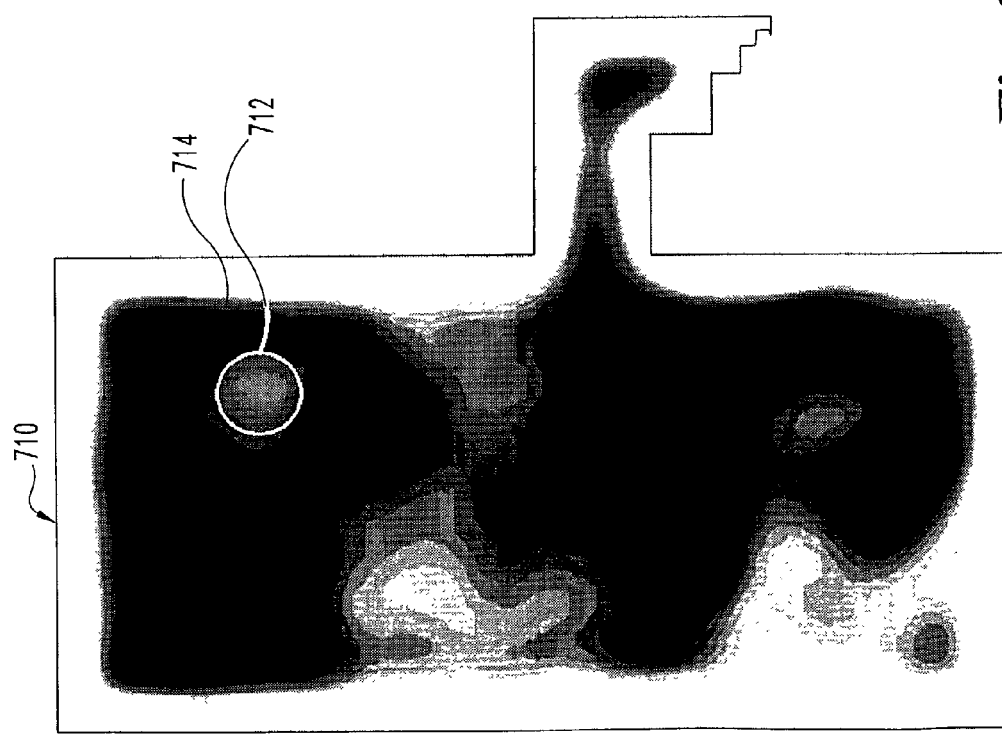

From stage 134, routine 120 proceeds to conditional 136 to test whether further sequence processing is desired. If more testing is desired, routine 120 returns to stage 122 to select/access sequence data. Nonlimiting examples relating to the processing of different sequences are provided in FIG. 20. FIG. 20 provides gray-scale representations of chromatically colored visualizations 710 and 720 of the MC 58 and Z2491 N. meningitides genomes, respectively. Visualizations 710 and 720 were generated by performing realignment and enhancements in accordance with routine 120. As indicated by the open circle added to visualization 710, feature 712, corresponding to an orange-red spot, appears in the upper right side, but is absent in visualization 720. Feature 712 is surrounded by dark region 714 of visualization 710 for which there is a comparable dark region 724 in visualization 720. The contrasting coloration of feature 712 relative to regions 714 and 724 tends to readily direct the eye of an observer to it. The distinctiveness of feature 712 indicates that no homologous region is present in strain Z2491. The DNA sequences corresponding to feature 712 in visualization 710 were retrieved and used to match against the entire genomic sequence of the Z2491 strain utilizing BLAST sequence similarity searching. The results indicate that no homologous region corresponding to feature 712 is found in strain Z2491. Accordingly, feature 712 is likely to correspond to a region of novel sequencing of strain MC 58 in relation to strain Z2491.

It has also been advantageously discovered that more than two genome visualizations can be simultaneously compared. In contrast, sequence alignment tools such as BLAST or various dot matrix techniques only provide for comparison of two sequences at a time. Examples of the dot matrix approach are described by authors J. Pustell and F. C. Kafatos in *A Convenient and Adaptable Package of Computer Programs for DNA and Protein Sequence Management, Analysis, and Homology Determination, Nucleic Acids Research*, Vol. 12, pages 643–655 (published 1984).

Figure 21:
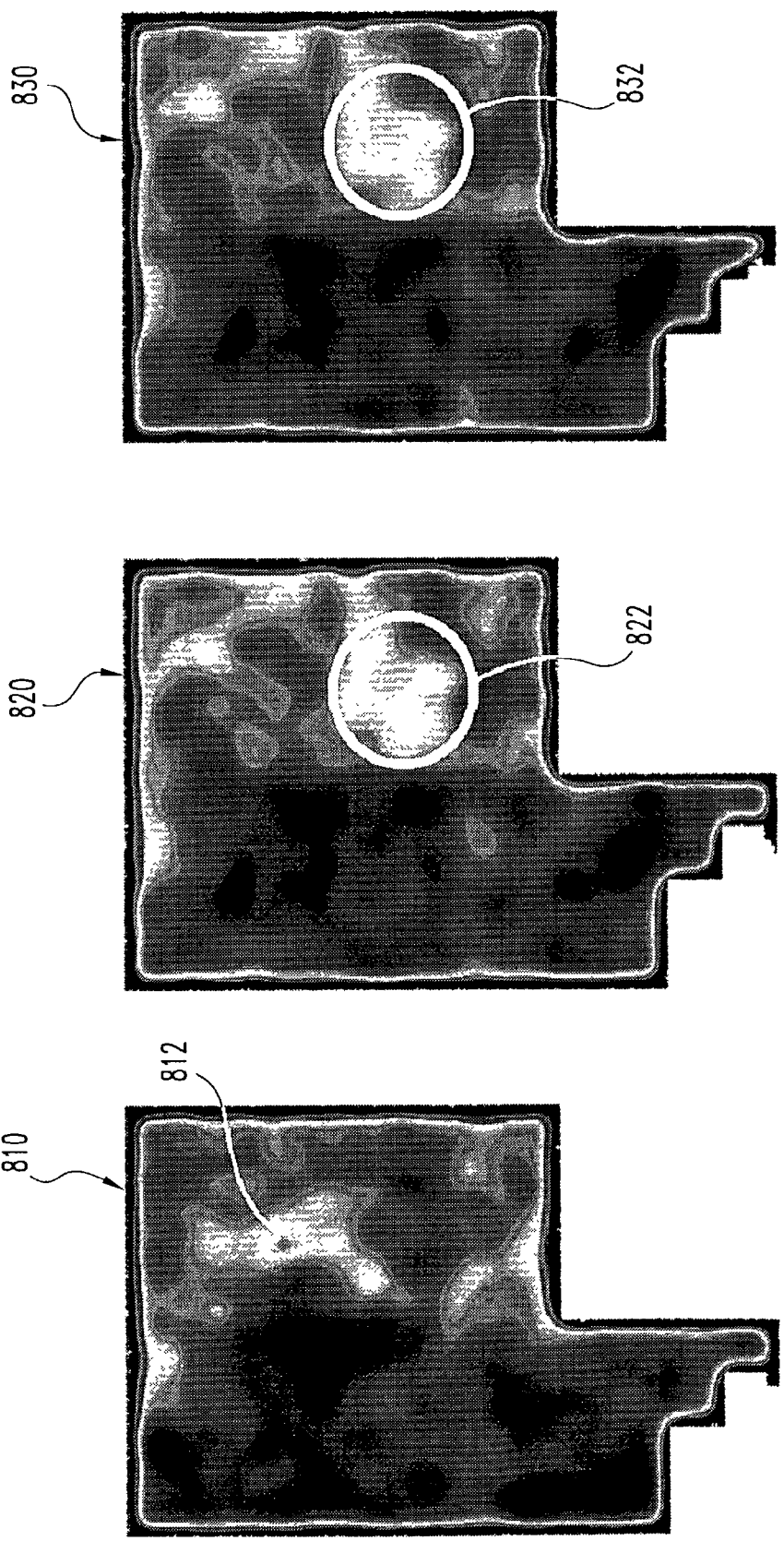
FIG. 21 is a comparative view of three computer-generated, gray scale representations of chromatically colored visualizations for yet three other bacteria genomes generated with the process of FIG. 2.

One nonlimiting example of a simultaneous comparison between three genomic visualizations is found in FIG. 21. Visualizations 810, 820, and 830 of FIG. 21 correspond to the genomes of three strains of *C. pneumoniae* AR39, CWL029, and J138 respectively. Visualizations 810, 820, and 830 were generated in accordance with routine 120 through stage 130. For visualization 810, 820, and 830 the darker regions correspond to a mottled brown and gray color while the lighter regions correspond to blue, green, and blue-green coloration. Furthermore, feature 812 of visualization 810 for the AR39 sequence corresponds to a magenta-colored dot surrounded by blue and green that appears to be unique in comparison to visualizations 820 and 830. Furthermore, visualization 820 and 830 both include a similarly shaped blue-green feature 822 and 832, respectively. Features 822 and 832 are enclosed in a white circle overlaid on the respective visualization 820 and 830. An analogous region in visualization 810 appears to be absent.

To verify similarity between features 822 and 832, DNA segments were extracted from the original genome sequences comprised of about 98,304 nucleotides and an alignment test was conducted with the ClustalW program, resulting in about a 99% match. Further, the circled 98,304-nucleotide long segment corresponding to feature 832 was compared against the entire AR29 genome sequence of approximately 1.2 million nucleotides represented by visualization 810 using BLAST sequence similarity. This comparison indicated only fragmentary matches no greater than 519 nucleotides in length (generally less than 0.5 percent) with an identity level of no greater than 65 percent.

Referring back to routine 120 of FIG. 2, while the affirmative branch of conditional 136 is depicted as returning to stage 122, it should be appreciated that the affirmative branch of conditional 136 could return to any other stages of routine 120. Alternatively or additionally, conditional 136 could present multiple options to an operator as to the return point or points of routine 120. If the test of conditional 136 is negative, routine 120 halts.

The visualizations generated with routine 120 could be stored using computer equipment 21 in memory 28 and/or one or more of sources 50. Alternatively or additionally, comparisons between different visualizations can be performed by accessing stored visualizations. Furthermore, computer network 30 can be used to remotely access and/or control visualizations. In one alternative embodiment, a visualization service can be provided via a form of network 30 that includes the internet and/or visualization software or data could be distributed via the internet. Routine 120 can also include options to present visualizations with display 26a and/or printer 26b. Further, visualizations can be presented with chromatic coloration, achromatic coloration, a combination of both, and/or such different means of appearance differentiation as would occur to those skilled in the art.

Alternatively or additionally, image elements can each be arranged to represent two or more consecutive monomers of a sequence. By way of nonlimiting example, a single image element can represent three consecutive nucleotides of a nucleotide sequence. Such "nucleotide triplets" can correspond to codons of an intron.

It should further be understood that in alternative embodiments one or more of the image adjustments of routine 120 could be performed with computer equipment 21 before presenting the visualization. Further stages of routine 120 can be iteratively performed in response to changing a selection of one or more parameters by an operator. As such selections are made, different visualization results can be compared. In one form, a Graphic User Interface (GUI) is provided that permits sequence selection changes in stage 122, coloration changes in stage 124, spatial arrangement pattern selection in stage 126, filtering parameter and/or filter type selection (if any) in stage 128, enhancement routines/parameter selection in stage 130 and/or further processing options corresponding to conditionals 132 and 136, simultaneously, utilizing the same equipment 21. GUI selection can be input by an operator with one or more of devices 24. GUI techniques can also be used to facilitate storage and presentation of visualizations in one or more forms. Indeed, it should be understood that in other embodiments, various stages and conditionals of routine 120 can be combined, performed in a different order, omitted, and/or added to other routine(s) as would occur to those skilled in the art.

Alternatively or additionally, different visualizations can be provided in different windows on display 26a that can be separately scaled, opened, or closed. Optionally, a zoom-in/zoom-out tool can be provided to rescale a visualization and/or portion of a visualization based on operator input with one or more of devices 24, and/or otherwise perform different imaging operations. In one embodiment, coloration enhancement is targeted through operator selection of specified area(s) of a visualization. In another embodiment, different image element patterns and/or appearances are used in different visualization areas.

According to other embodiments of the present invention, only a portion of a sequence may be displayed at one time or a sequence may be displayed on multiple pages and/or windows. In still other embodiments, only a portion of a sequence is selected for processing initially. Alternatively or additionally, besides genetic sequences corresponding to DNA or RNA, other biopolymer sequences of native or non-native types can be visualized in accordance with the present invention. For example, a visualization of a protein sequence of amino acids can be generated in accordance with the present invention. In another example, a visualization of the biopolymer, lignin, comprised of a sequence of syringyl and guaiacyl monomers can be provided. In yet another example, other biopolymers such as cellulose, polysaccharides, and fatty acids are visualized with routine 120 instead of a nucleotide sequence. In still other embodiments of the present invention, a polymer sequence of monomer units of differing types can be visualized, including monomers and/or polymers of a synthetic or nonbiological type.

Figure 22:
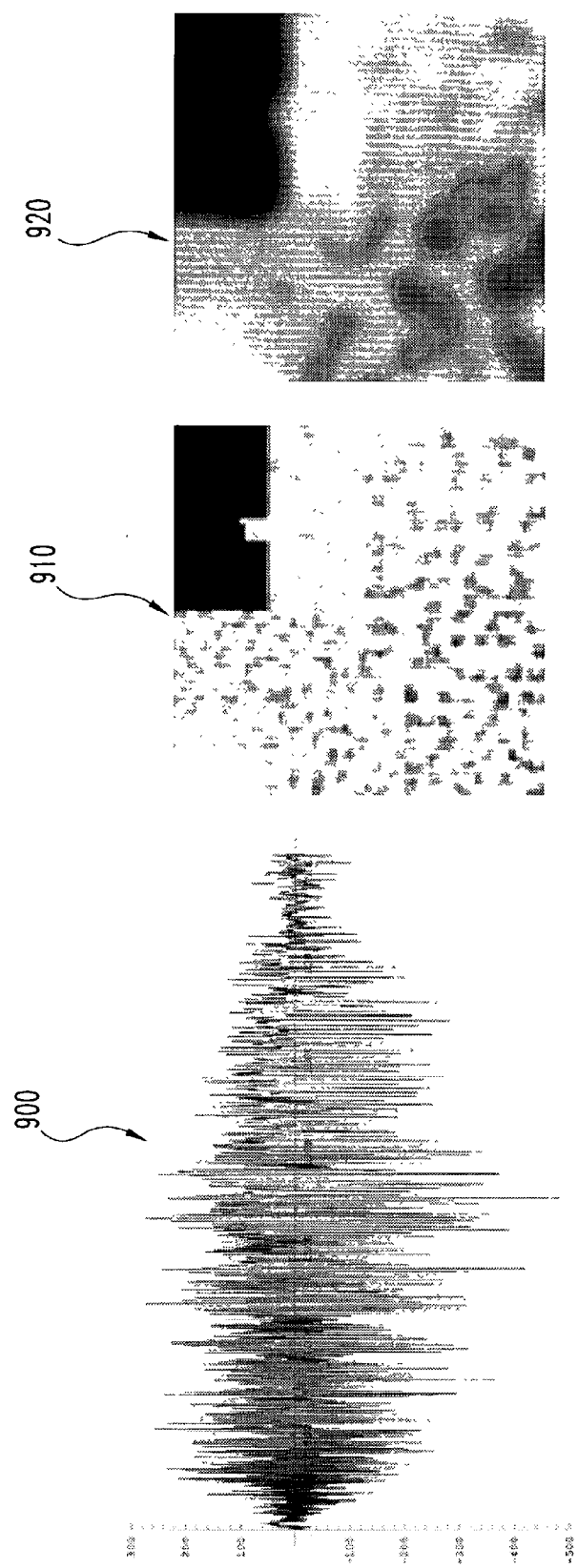
FIG. 22 is a comparative view of a line plot of several electroencephalogram (EEG) recordings of electrical activity of a patients brain during a seizure and two computer-generated gray scale representations of chromatically colored visualizations corresponding to the EEG recordings that were generated with the process of FIG. 2.

Besides polymer sequencing information, visualization of other data with an "a priori" order can advantageously be provided in accordance with the teachings of the present invention. For example, various forms of time-series data having many sequence units could benefit from this kind of visualization approach. Referring to FIG. 22, a nonlimiting example of time-series data is provided in the form of a set of electroencephalogram (EEG) recordings in graph 900. These recordings correspond to electric signals of the brain as detected by monitoring equipment. Specifically, graph 900 provides a line plot of 3600 EEG recordings from an electrode attached to a patient's scalp during a seizure. These readings were measured in microvolts and taken every one fortieth ($\frac{1}{40}^{th}$) of a second. Visualization 910 reformats the EEG information from graph 900 by applying a Hilbert curve pattern with a hot-temperature chromatic color mapping as described in connection with routing 120. FIG. 22 presents visualization 910 in a gray scale form. The darkest region of visualization 910 appears in the upper right hand corner and corresponds to an unused area of the respective Hilbert curve square. The lightest regions of visualization 910 correspond to a yellow coloration and the intermediate gray shades of visualization 910 correspond to red and orange coloration. Visualization 920 of FIG. 22 is provided in a gray scale form, and represents visualization 910 after enhancement in accordance with stages 128 and 130 of routine 120. In visualization 920, the lightest regions correspond to a mottled yellow coloration in the upper left and in the upper right below the unused darkest region. These yellow-colored areas correspond to the initial and final stages of the seizure. In the lower half of visualization of 920, the darkest regions correspond to a blue coloration that have some of the lowest measurement values. The intermediate shades of gray correspond to a mottled red, orange, or pink coloration. It should be understood that EEG recordings are just one example of a nonpolymer application of the teachings of the present invention, and that many other forms of time-series data or other information with an "a priori" order could be visualized in accordance with the present invention.

One form of the present invention includes: visualizing a large quantity of ordered information by spatially arranging image elements in accordance with the order. In one variation, this spatial arrangement corresponds to a fractal with a fractal dimension of at least two, such as a Moore curve or Hilbert curve, to name just a few examples. The ordered information can correspond to a polymer sequence of different monomer unit types, time-series data, or another form as would occur to those skilled in the art. This form may further include performing one or more enhancements to group various features of the information visually.

A further form is a method that includes: generating a visualization of information having an "a priori" order, and representing this information with a sequence of image elements spatially ordered in accordance with a repeating folded line segment pattern. This information can correspond to time-series data and/or a polymer sequence comprised of different monomer units. Alternatively or additionally, the repeating folded line segment pattern can correspond to a turning path where one portion of the path progresses in a first direction and another portion of the path progresses in a second direction opposite the first direction. Systems, apparatus, and devices to carryout this method are among other embodiments of the present invention.

Still a further form of the present invention is a method that includes: selecting a display pattern to represent information having an "a priori" order that corresponds to a fractal with a fractal dimension of at least two, and at least partially filling a matrix of display locations in accordance with the display pattern to visualize the information. The information can correspond to time-series data and/or a polymer sequence comprised of different monomer units. Systems, apparatus, and devices to carryout this method are included among other embodiments of the present invention.

In another form of the present invention, a method includes: selecting a biopolymer sequence of at least 100,000 monomer units; displaying an image to represent the sequence that includes at least 100,000 image elements spatially ordered in correspondence to the order of the sequence (where such elements each represent at least one of the monomer units and vary in color with different types of the monomer units); and adjusting one or more color parameters of the image as a function of the elements to visually distinguish different segments of the sequence. Systems and apparatus to carry out this method are included among other embodiments of the present invention.

In yet another form of the present invention, a method includes: providing a visualization of a biopolymer sequence of monomer units with a number of image elements that each correspond to at least one of the monomer units and differ in color with different types of the monomer units; and arranging the image elements in the visualization in a spatial order corresponding to monomer unit order of the sequence. The spatial order progresses in accordance with a line segment pattern repeated several times within the visualization. Systems and apparatus to carry out this method are also among other embodiments of the present invention.

In still another form of the present invention, a device carries instructions executable with computer equipment to generate a visualization of a biopolymer sequence of monomer units and represent the monomer units with a sequence of image elements spatially ordered in accordance with a repeating folded line segment pattern. Alternatively or additionally, the instructions provide for the arrangement of image elements in a spatial order that progresses relative to a turning path where one portion of the path proceeds in a first direction and another portion of the path proceeds in a second direction opposite the first direction. In still another form, such apparatus can carry instructions arranged to select a display pattern to represent a biopolymer sequence that corresponds to a fractal with a fractal dimension with at least two and at least partially fill a matrix of display locations in accordance with the pattern to visualize the biopolymer sequence.

For another form, a system of the present invention includes one or more processors operable to access data representative of a biopolymer sequence of monomer units and generate one or more output signals corresponding to a visualization of the biopolymer sequence, such that the sequence and monomer units are represented in the visualization with a sequence of image elements spatially ordered in accordance with a repeating folded line segment pattern. Alternatively or additionally, the processor provides one or more signals to arrange image elements in a spatial order that progresses relative to a turning path where one portion of the path proceeds in a first direction and another portion of the path proceeds in a second direction opposite the first direction. Still another form of a system according to the present invention can include computer equipment operable to select a display pattern to represent a biopolymer sequence that corresponds to a fractal with a fractal dimension of at least two and to at least partially fill a matrix of display locations in accordance with this pattern to visualize the sequence.

In another embodiment, computer equipment is configured to select a sequence of nucleotide bases; provide a visualization of the sequence of nucleotide bases with a corresponding sequence of image elements that each correspond to one of the bases and vary in color with different nucleotide base types. The visualization includes a first area with one coloration surrounded by a second area with a different coloration. The first area represents one sequence segment of at least 1,000 nucleotide bases and the second area represents one or more other sequence segments of the nucleotide bases.

Yet a further embodiment of the present invention includes computer equipment operable to perform the method comprising: displaying a first visualization that includes a first image element sequence to represent a nucleotide base sequence defining a first genome; displaying a second visualization including a second image element sequence to represent another nucleotide base sequence defining a second genome; comparing the first and second visualizations; and realigning one of the first image element sequence and the second image element sequence based on this comparison.

While the invention has been illustrated and described in detail in the drawings and foregoing description, the same is to be considered illustrative and not restrictive in character, it being understood that only the preferred embodiment has been shown and described and that all changes, equivalents, and modifications that come within the scope of the inventions described herein or defined by the following claims are desired to be protected. Any experiments, experimental examples, or experimental results provided herein are intended to be illustrative of the present invention and should not be construed to limit or restrict the invention scope. Further, any theory, mechanism of operation, proof, or finding stated herein is meant to further enhance understanding of the present invention and is not intended to limit the present invention in any way to such theory, mechanism of operation, proof, or finding. In reading the claims, words such as "a", "an", "at least on", and "at least a portion" are not intended to limit the claims to only one item unless specifically stated to the contrary. Further, when the language "at least a portion" and/or "a portion" is used, the claims may include a portion and/or the entire item unless specifically stated to the contrary.

What is claimed is:

1. A method, comprising:

selecting a biopolymer sequence of at least 100,000 monomer units;

displaying an image to represent the sequence, the image including at least 100,000 image elements spatially ordered in correspondence to monomer unit order of the sequence and in accordance with a pattern corresponding to a repeating folded line segment path, the elements each representing at least one of the monomer units and varying in color in correspondence to variation in monomer unit type;

adjusting one or more color parameters of the image as a function of the elements to visually distinguish different segments of the sequence; and filtering image data as a function of the elements to provide filtered image data, wherein the image is based on the filtered image data and wherein the filtering removes obscuring information from the image such that the image is capable of display in a smaller image area than an image based on the image data.

2. The method of claim 1, wherein the color of the elements varies chromatically and the elements are each provided in the form of at least one pixel.

3. The method of claim 1, wherein said adjusting is performed before the image is displayed.

4. The method of claim 1, wherein the one or more parameters correspond to one or more equalization histograms.

5. The method of claim 1, wherein the one or more parameters include at least one of image contrast and image saturation.

6. The method of claim 1, wherein spatial ordering of the elements is provided in accordance with a pattern corresponding to a repeating folded line segment path.

7. The method of claim 6, wherein the pattern corresponds to a Hilbert curve.

8. The method of claim 1, wherein the image elements each represent consecutive segments of two or more of the monomer units.

9. The method of claim 1, wherein the sequence represents at least a portion of a genome, a protein, or a lignin.

10. The method of claim 1, wherein the biopolymer sequence is a first genetic sequence, the monomer units number at least 1,000,000 and are each a nucleotide base, and the image elements number at least 1,000,000, and further comprising:

generating an image representative of a second genetic sequence;

adjusting the one or more color parameters of the image representative of the second genetic sequence;

comparing the image representative of the first genetic sequence and the image representative of the second genetic sequence after said adjusting; and aligning the first genetic sequence with the second genetic sequence based on said comparing.

11. A method, comprising:

selecting a biopolymer sequence of at least 100,000 monomer units, the monomer units each being one of a number of different types;

providing a visualization image including at least 100,000 image elements to represent the sequence, the image elements each representing at least one of the monomer units with one of a number of appearances that vary in accordance with variation of monomer unit type; and spatially ordering the image elements in the visualization image in accordance with monomer unit order of the sequence and in accordance with a pattern corresponding to a convoluted line segment path;

wherein a filter is applied to substantially all of the visualization image to yield a smoothed visualization image.

12. The method of claim 11, wherein the appearances are each a different chromatic or achromatic color.

13. The method of claim 12, wherein the image elements each correspond to three consecutive monomer units.

14. The method of claim 12, wherein the biopolymer sequence represents at least a portion of a genome, a protein, or a lignin.

15. The method of claim 12, wherein at least a portion of the pattern corresponds to a fractal with a fractal dimension of at least two.

16. The method of claim 11, wherein said selecting includes accessing a database with computer equipment to process information corresponding to the biopolymer sequence and said providing includes:

generating one or more corresponding output signals with the equipment; and displaying the image with an output device responsive to the one or more output signals, the output device including a display area defined by a number of rows each including a number of pixels, and the image elements are each in the form of at least one of the pixels.

17. The method of claim 11, wherein the biopolymer sequence corresponds to at least a portion of a genetic sequence of one type of bacteria, the monomer units number at least 1,000,000 and are each a nucleotide base, and which further includes comparing the image to another image representative of a genome of another type of bacteria.

18. A method, comprising:
generating a first visualization of a biopolymer sequence of monomer units; and
representing the sequence of the monomer units in the first visualization with a first sequence of image elements spatially ordered in accordance with a repeating folded line segment pattern;
wherein substantially all of the first visualization is filtered to reduce high frequency visual content that is attributable to the number of and variations between the image elements.

19. The method of claim 18, wherein the pattern corresponds to a shape-filling curve.

20. The method of claim 19, wherein the shape-filling curve is of a Hilbert type and the image elements are each in the form of one or more pixels.

21. The method of claim 18, wherein the biopolymer sequence corresponds to at least a portion of a genome, a protein, or a lignin.

22. The method of claim 18, wherein the image elements differ in color in correspondence to variation of monomer unit type.

23. The method of claim 18, wherein the biopolymer sequence corresponds to a first genetic sequence of one type of bacteria, the monomer units number at least 1,000,000 and are each a nucleotide base, the image elements number at least 1,000,000 and vary in color according to different nucleotide base types, and which further includes:
displaying a second visualization corresponding to a second genetic sequence of another type of bacteria, the second genetic sequence including at least 1,000,000 nucleotide bases;
performing a comparison of the first visualization and the second visualization; and
aligning the first genetic sequence and second genetic sequence based on the comparison.

24. The method of claim 23, wherein the second genetic sequence is represented by a second sequence of image elements arranged in accordance with the repeating folded line segment pattern.

25. The method of claim 24, wherein the pattern corresponds to a fractal with a fractal dimension of at least two.

26. The method of claim 25, wherein the first sequence of image elements and the second sequence of image elements are assigned color in accordance with variation of nucleotide base type being represented.

27. The method of claim 26, which includes identifying a first segment of the first genetic sequence and a second segment of the second genetic sequence and performing said aligning as a function of the first and second segments, the first and second segments having a percent identity of at least 70%.

28. A method, comprising:
displaying an image including several image elements to visualize a biopolymer sequence of monomer units, the image elements each representing at least one of the monomer units and varying in color relative to variation of monomer unit type; and
arranging the image elements in a spatial order that progresses relative to a turning path, one portion of the path progressing in a first direction and another portion of the path progressing in a second direction opposite the first direction;
wherein substantially all of the image has been filtered to reduce high frequency visual content that is attributable to the number of and variations between the image elements.

29. The method of claim 28, wherein the biopolymer sequence is genetic, the monomer units number at least 1,000,000 and are each one of four different nucleotide base types, the image elements number at least 1,000,000, and the color of the image elements varies chromatically with the four different nucleotide base types.

30. The method of claim 28, which includes adjusting coloration of at least a portion of the image elements in accordance with one or more equalization histograms.

31. The method of claim 30, wherein the folded line segment corresponds to a shape-filling curve.

32. The method of claim 31, wherein the shape-filling curve is of a Hilbert type.

33. The method of claim 28, wherein the biopolymer sequence corresponds to at least a portion of a genome, a protein, or a lignin.

34. The method of claim 28, wherein the image elements each represent consecutive sequence segments, the consecutive sequence segments are each comprised of two or more of the monomer units, and the image elements each correspond to a different pixel of the image.

35. The method of claim 28, wherein the path includes two other portions, a first one of the other portions progresses in a third direction, a second one of the other portions progresses in a fourth direction opposite the third direction, and the third direction and the fourth direction are approximately perpendicular to the first direction and the second direction.

36. The method of claim 35, wherein at least a portion of the path progresses from the first direction to the third direction, from the third direction to the second direction, and from the second direction to the fourth direction.

37. An apparatus, comprising: a device carrying instructions executable with computer equipment to: access data corresponding to a biopolymer sequence of at least 100,000 monomer units; represent the sequence with at least 100,000 image elements each corresponding to one of the monomer units and varying in color in correspondence to variation of monomer unit type; filter image data to reduce high frequency visual content; and display a smoothed image based on the filtered image data and including the image elements arranged in a repeating folded line segment pattern to visualize the sequence.

38. The apparatus of claim 37, wherein the device is in the form of a removable memory encoded with the instructions.

39. The apparatus of claim 38, wherein the removable memory includes at least one storage disk.

40. The apparatus of claim 37, wherein the device is in the form of one or more components of a computer network.

41. The apparatus of claim 37, wherein the instructions are further executable to adjust one or more color parameters of the image to enhance visualization of different segments of the sequence.

42. A system, comprising:
one or more processors operable to access data representative of a biopolymer sequence of monomer units and generate one or more output signals corresponding to a pattern of image elements each representative of at least one of the monomer units with color of the image elements varying to correspond to variation in monomer unit type, the pattern spatially ordering the image elements in correspondence to monomer unit order of the sequence, the pattern corresponding to a repeating folded line segment, the pattern having been filtered such that substantially all of the resulting image is smoothed relative to an unfiltered image; and a device responsive to the one or more output signals to display the image elements in accordance with the pattern to visualize the biopolymer sequence.

43. The system of claim 42, further comprising a memory storing the data and programming instructions executable with the one or more processors to generate the one or more output signals.

44. The system of claim 42, wherein the device is a graphic computer monitor display arranged with a matrix of pixels, the image elements each correspond to a different set of one or more of the pixels, and the pattern places each of the image elements next to another of the image elements in accordance with the monomer unit order of the sequence.

45. The system of claim 42, wherein the device is a graphic printer.

46. The system of claim 42, wherein the pattern corresponds to a shape-filling curve and the image elements each correspond to a different pixel displayed with the device.

47. A system, comprising:
means for accessing information having an a priori order, the information corresponding to at least one of time-series data and a polymer sequence of monomer units of different types;
means for determining a sequence of image elements in correspondence to the order of the information;
means for filtering as a function of the image elements, wherein the filtering is applied across substantially all of the image elements to remove high frequency visual content;
means for adjusting one or more color parameters of the image elements; and
means for displaying the image elements in accordance with a pattern including a folding line pattern and corresponding to a fractal with a fractal dimension of at least two.

48. A method, comprising:
selecting a display pattern to represent a biopolymer sequence, the display pattern including a folding line pattern and corresponding to a fractal with a fractal dimension of at least two; and
at least partially filling a matrix of display locations in accordance with the display pattern to visualize the biopolymer sequence;
wherein the visualization is based on image data from which high frequency visual content attributable to the number of and variations between different segments of the sequence has been removed by filtering applied across the visualization.

49. The method of claim 48, wherein the fractal corresponds to at least one of a Hilbert curve and a Moore curve.

50. The method of claim 48, wherein the fractal has a self-similarity based on a 2 by 2 matrix.

51. The method of claim 48, wherein the biopolymer sequence is comprised of a number of monomer units each being one of two or more types, and said at least partially filling the matrix includes representing each of the monomer units with a corresponding one of a number of image elements, the image elements each having one of a number of different appearances, the different appearances each representing a different one of the two or more types.

52. The method of claim 51, wherein the image elements each correspond to one or more different pixels, the biopolymer sequence is genetic, the monomer units number at least 100,000 and are each one of four different nucleotide base types, the image elements number at least 100,000, and the different appearances each correspond to a different chromatic coloration.

53. The method of claim 52, which includes adjusting color of at least a portion of the image elements in accordance with one or more equalization histograms.

54. A method, comprising:
selecting a sequence of nucleotide bases;
providing a visualization of the sequence of nucleotide bases with a corresponding sequence of image elements arranged in a folding line pattern, the image elements each corresponding to at least one of the bases and varying in color with variation of different nucleotide base types; and
wherein the visualization includes a first area with one coloration surrounded by a second area of a different coloration, the first area representing one sequence segment of at least 1000 nucleotide bases and the second area representing one or more other sequence segments of the nucleotide bases;
wherein at least the first and second areas of the image have been filtered to remove high frequency visual content.

55. The method of claim 54, further comprising selecting the one segment for further evaluation.

56. The method of claim 55, which includes comparing the visualization to another visualization for another genetic sequence and determining a genetic sequence alignment based on the one segment.

57. The method of claim 54, wherein said providing includes arranging the image elements in a spatially ordered pattern corresponding to a fractal with a fractal dimension of at least two.

58. The method of claim 54, wherein the image elements are each in the form of one or more pixels, and said providing includes adjusting the color of at least a portion of the image elements in correspondence with an equalization histogram.

59. A method, comprising:
displaying a first visualization including a first image element sequence including a folding line pattern to represent a nucleotide base sequence defining a first genome;
displaying a second visualization including a second image element sequence including a folding line pattern to represent another nucleotide base sequence defining a second genome;
comparing the first visualization and the second visualization; and
realigning one of the first image element sequence and the second image element sequence based on said comparing
wherein at least the portions of interest in the first and second visualizations have been smoothed.

60. The method of claim 59, wherein the first image element sequence and the second image element sequence are each displayed in a spatial pattern corresponding to a fractal with a fractal dimension of at least two.

61. The method of claim 59, wherein the first image element sequence and the second image element sequence are each comprised of image elements with coloration corresponding to variation in different nucleotide base types.

62. The method of claim 61, wherein the image elements are each in the form of one of more pixels and which includes determining coloration of the first visualization and the second visualization in accordance with at least one of: histogram equalization, contrast stretching, and saturation adjustment.

63. The method of claim 59, wherein the first genome and the second genome are each of a different type of bacteria.

64. The method of claim 59, wherein said comparing includes identifying a first segment of the first genome and a second segment of the second genome based on a common appearance of a first region of the first visualization and a second region of the second visualization, the first segment and the second segment having a percent identity of at least 70%.

65. The method of claim 64, wherein the common appearance includes a common coloration of the first region and the second region.

66. The method of claim 59, which includes displaying a third visualization including a third image element sequence to represent a further nucleotide base sequence defining a third genome.

67. The method claim 59, which includes filtering a first image data set to provide the first visualization and a second image data set to provide the second visualization, and wherein said displaying the first visualization and said displaying the second visualization include presenting the first visualization and the second visualization simultaneously for a period of time with the same graphic computer monitor display.

68. A method, comprising:
displaying a first visualization including a first image element sequence including a folding line pattern to represent a nucleotide base sequence defining a first genome;
displaying a second visualization including a second image element sequence including a folding line pattern to represent a second nucleotide base sequence defining a second genome;
displaying a third visualization including a third image element sequence including a folding line pattern to represent a third nucleotide base sequence defining a third genome; and
wherein said displaying the first visualization, said displaying the second visualization, and said displaying the third visualization occur simultaneously for a period of time on a graphic computer monitor display;
wherein at least portions of interest in the first, second and third visualization have been filtered to remove obscuring high frequency visual content.

69. The method of claim 68, which includes comparing the first visualization, the second visualization, and the third visualization to visually identify one or more sequence segments of interest.

70. The method of claim 69, which includes selecting a realignment reference point based on said comparing.

71. The method of claim 68, wherein the first genome, the second genome, and the third genome are each a different type of bacteria.

72. The method of claim 68, which includes generating the first visualization, the second visualization, and the third visualization in accordance with a fractal pattern having a fractal dimension of at least two.

73. The method of claim 72, which includes enhancing one or more color parameters of the first visualization, the second visualization, and the third visualization.

74. The method of claim 68, which includes displaying one or more other visualizations each having a corresponding image element sequence to represent a different genome and wherein said displaying the first visualization, said displaying the second visualization, said displaying the third visualization, and said displaying the one or more other visualizations occur simultaneously for the period of time on the graphic computer monitor display.

75. A method, comprising:
creating a visualization of a large quantity of data having an established order by:
generating image data corresponding to a spatial arrangement of the data in accordance with the established order along a path comprising a repeating folded line segment; and
performing a convolution operation on the image data to remove obscuring visual information from at least a visualization portion of interest, the removed information being at least partially attributable to the large quantity of the data.

76. The method of claim 75, further comprising adjusting one or more color parameters of the visualization.

77. The method of claim 76, wherein the convolution operation is a 2-D filtering operation selected from Gaussian filtering, highpass filtering, notch filtering, bandpass filtering, and median filtering.

78. The method of claim 76 wherein adjusting one or more color parameters of the visualization includes at least one of: histogram equalization, contrast stretching, and saturation adjustment.

79. The method of claim 76 wherein the data is time series data.

80. The method of claim 79 wherein the time series data corresponds to electrical signals detected by monitoring equipment.

81. The method of claim 75, further comprising selecting at least a portion of the visualization portion of interest for further processing.

82. The method of claim 81, further comprising realigning the data based on the selected portion of the visualization portion of interest.

83. The method of claim 81, further comprising comparing at least the selected portion of the visualization portion of interest with second visualization of a second quantity of data.

84. The method of claim 83 further comprising selecting a realignment reference point in the selected portion of the visualization portion of interest.

85. The method of claim 75 wherein the data includes polymer sequence information.

86. The method of claim 75 wherein the path comprises a fractal.

87. The method of claim 86 wherein performing the convolution operation removes high frequency content from substantially all of the visualization.

88. The method of claim 76 wherein performing the convolution operation removes high frequency content from substantially all of the visualization.

* * * * *

SEQUENCE LISTING

<160> NUMBER OF SEQ ID NOS: 4

<210> SEQ ID NO 1
<211> LENGTH: 16
<212> TYPE: DNA
<213> ORGANISM: Artificial Sequence
<220> FEATURE:
<223> OTHER INFORMATION: Fictional sequence created for purposes of
      illustration

<400> SEQUENCE: 1
acgtacgtac gtacgt                                                     16

<210> SEQ ID NO 2
<211> LENGTH: 242
<212> TYPE: DNA
<213> ORGANISM: Neisseria meningitidis

<400> SEQUENCE: 2
aaacaacaaa caacaaacaa caaacaacaa acaacaaaca acaaacaaca aacaacaaac      60
aacaaacaac aaacaacaaa caacaaacaa caaacaacaa acaacaaaca acaaacaaca     120
aacaacaaac aacaaacaac aaacaacaaa caacaaacaa caaacaacaa acaacaaaca     180
acaaacaaca aacaacaaac aacaaacaac aaacaacaaa caacaaacaa caaacaacaa     240
ac                                                                   242

<210> SEQ ID NO 3
<211> LENGTH: 186
<212> TYPE: DNA
<213> ORGANISM: Neisseria meningitidis

<400> SEQUENCE: 3
aaacaacaaa caacaaacaa caaacaacaa acaacaaaca acaaacaaca aacaacaaac      60

```
aacaaacaac aaacaacaaa caacaaacaa caaacaacaa acaacaaaca acaaacaaca    120
aacaacaaac aacaaacaac aaacaacaaa caacaaacaa caaacaacaa acaacaaaca    180
acaaac                                                               186

<210> SEQ ID NO 4
<211> LENGTH: 7
<212> TYPE: DNA
<213> ORGANISM: Neisseria meningitidis

<400> SEQUENCE: 4 aaacaac                                                              7
```